United States Patent
Alt et al.

(10) Patent No.: US 10,538,767 B2
(45) Date of Patent: *Jan. 21, 2020

(54) PREVENTING TUMOR DEVELOPMENT AND METASTASIS

(71) Applicant: The Administrators of the Tulane Educational Fund, New Orleans, LA (US)

(72) Inventors: Eckhard Alt, New Orleans, LA (US); Reza Izadpanah, New Orleans, LA (US)

(73) Assignee: The Administrators of the Tulane Educational Fund, New Orleans, LA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/200,508

(22) Filed: Nov. 26, 2018

(65) Prior Publication Data

US 2019/0078092 A1   Mar. 14, 2019

Related U.S. Application Data

(63) Continuation-in-part of application No. 14/814,130, filed on Jul. 30, 2015, now Pat. No. 10,137,143.

(60) Provisional application No. 62/031,021, filed on Jul. 30, 2014.

(51) Int. Cl.
| | |
|---|---|
| *C07H 21/04* | (2006.01) |
| *C12N 15/113* | (2010.01) |
| *A61K 31/7105* | (2006.01) |
| *A61K 47/68* | (2017.01) |
| *A61P 35/04* | (2006.01) |
| *A61P 35/00* | (2006.01) |
| *A61K 31/713* | (2006.01) |

(52) U.S. Cl.
CPC .......... *C12N 15/113* (2013.01); *A61K 31/713* (2013.01); *A61K 31/7105* (2013.01); *A61K 47/6851* (2017.08); *A61P 35/00* (2018.01); *A61P 35/04* (2018.01); *C12N 15/1135* (2013.01); *C12N 2310/11* (2013.01)

(58) Field of Classification Search
None
See application file for complete search history.

*Primary Examiner* — Kimberly Chong
(74) *Attorney, Agent, or Firm* — Boulware & Valoir

(57) ABSTRACT

Treatment of tumors, especially breast cancer or glioblastoma tumors, by silencing RAB27A and/or TRAF3IP2, compositions and methods for same.

21 Claims, 17 Drawing Sheets

Specification includes a Sequence Listing.

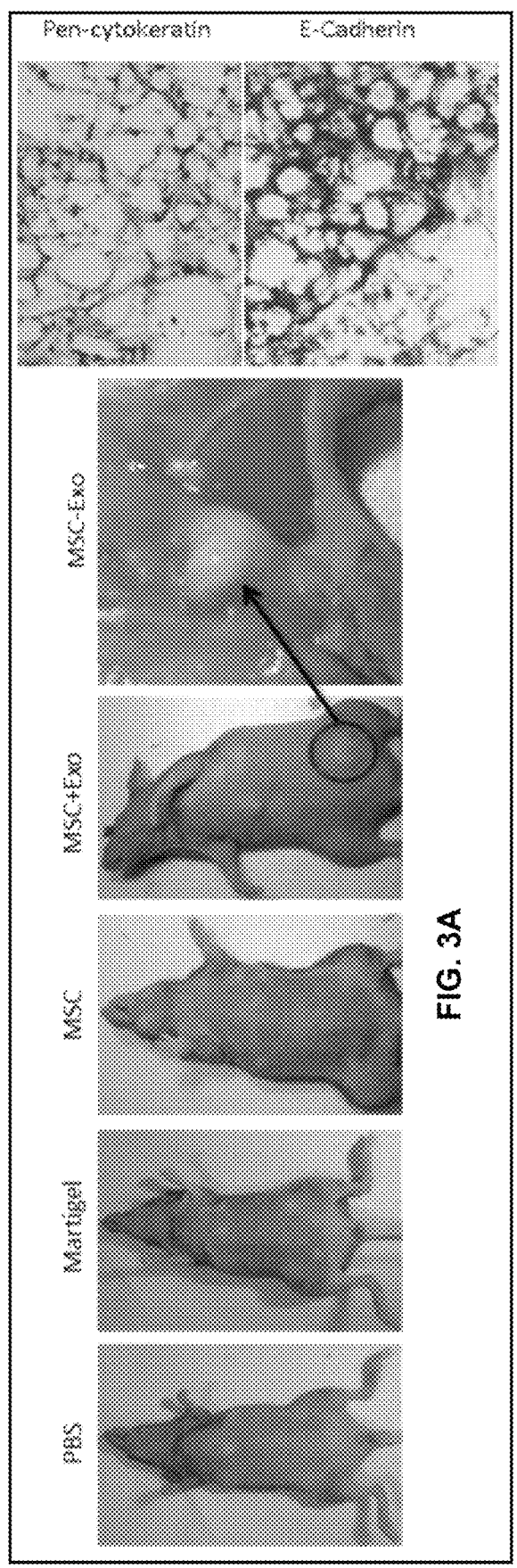
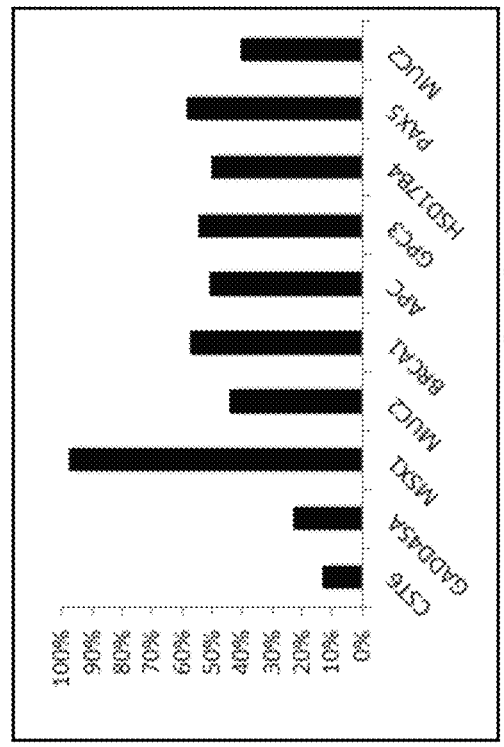
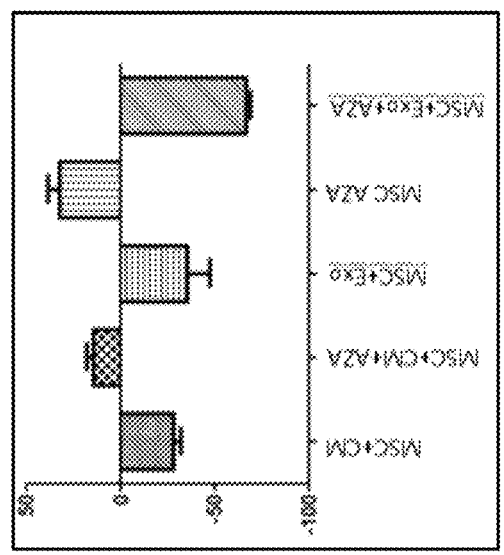
FIG. 3A
FIG. 3B
FIG. 3C

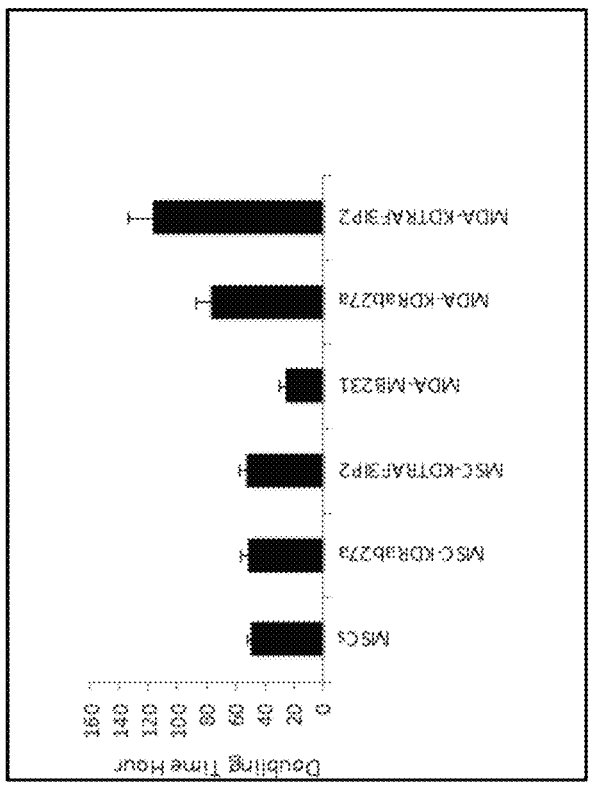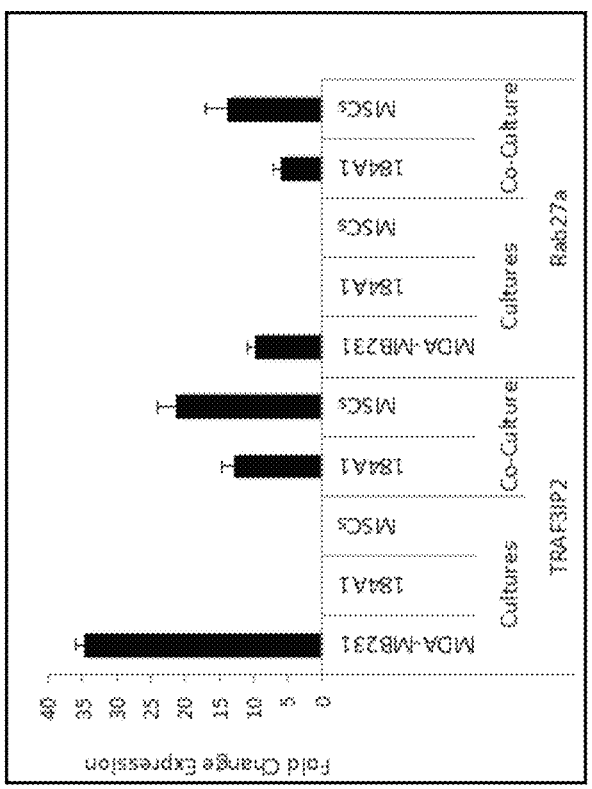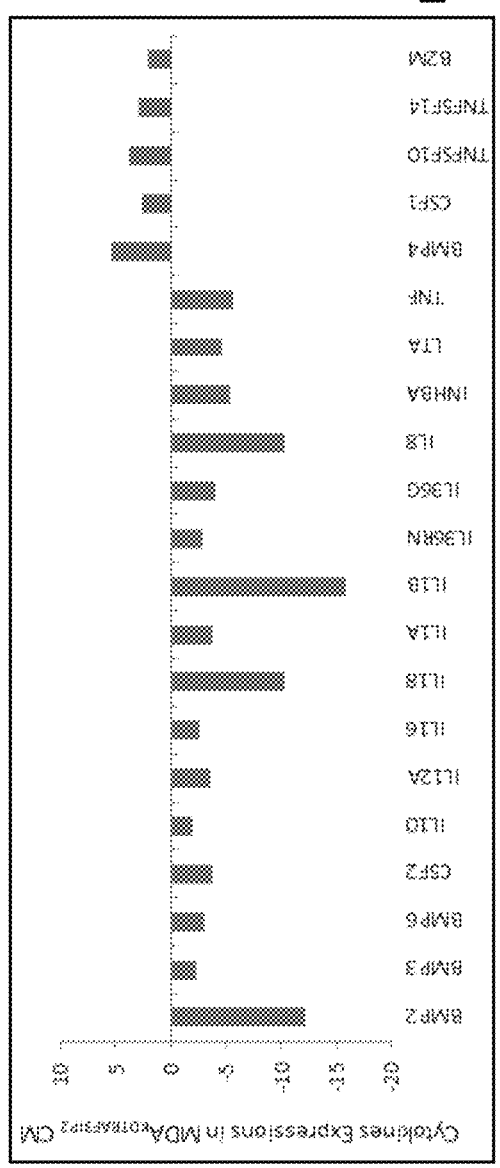
FIG. 4A
FIG. 4B
FIG. 4C

FIGURE 8

| Name | Sequence |
|---|---|
| RAB27A, variant 1 | NM_004580.4 (3,474 nt) |
| RAB27A, variant 2 | NM_183234.2 (3,455 nt) |
| RAB27A, variant 3 | NM_183235.2 (3,464 nt) |
| RAB27A, variant 4 | NM_183236.2 (3,415 nt) |
| RAB27A, variant X1 | XM_011521852.1 (3,663 nt) |
| RAB27A, variant X2 | XM_011521853.1 (3,744 nt) |
| RAB27A, variant X3 | XM_011521854.1 (3,536 nt) |
| RAB27A, variant X4 | XM_011521855.1 (3,528 nt) |
| RAB27A, variant X5 | XM_011521856.1 (3,314 nt) |
| RAB27A, variant X6 | XM_005254576.3 (3,342 nt) |
| TRAF3IP2 antisense RNA 1, variant 1 | NR_034108.1 (4,943 nt) |
| TRAF3IP2 antisense RNA 1, variant 2 | NR_034109.1 (4,652 nt) |
| TRAF3IP2 antisense RNA 1, variant 3 | NR_034110.1 (2,195 nt) |
| TTRAF3IP2 | NM_001164281.2 (6,241 nt) |
| TRAF3IP2, variant 2 | NM_147686.3 (6,244 nt) |
| | SEQ ID NO. 1: CCGGGCATGGAACTATCATTACCATTCTCGAGAATGGTAATGATAGTTCCATGTTTTT |
| HUMAN TRAF3IP2 SILENCER Variant 1: TRCN0000158477 | SEQ ID NO. 2 CCGGCCGTGATGATAATCGTAGCAACTCGAGTTGCTACGATTATCATCACGGTTTTTG |
| HUMAN TRAF3IP2 SILENCER Variant 2: TRCN0000005297 | SEQ ID NO. 3 CCGGGCTTCAGAACACTCATGTCTACTCGAGTAGACATGAGTGTTCTGAAGCTTTTTG |
| HUMAN TRAF3IP2 SILENCER Variant 3: TRCN0000160964 | SEQ ID NO 4: CCGGCGGATCAGTTAAGTGAAGAAACTCGAGTTTCTTCACTTAACTGATCCGTTTTT |
| HUMAN RAB27A SILENCER Variant 1: TRCN0000005296 | SEQ ID NO. 5: CCGGGCTGCCAATGGGACAAACATACTCGAGTATGTTTGTCCCATTGGCAGCTTTTT |
| HUMAN RAB27A SILENCER Variant 2: TRCN0000005297 | SEQ ID NO. 6: CCGGCCAGTGTACTTTACCAATATACTCGAGTATATTGGTAAAGTACACTGGTTTTT |
| HUMAN RAB27A SILENCER Variant 3: TRCN0000005295 | |

FIGURE 17B

ASO1 (SEQ ID NO. 13): mG*mG*mU*mG*mG*G*C*A*C*A*T*G*C*T*C*mC*mU*mU*mC*mU

ASO2 (SEQ ID NO. 14): mA*mG*mU*mG*mC*T*A*C*C*G*A*C*C*A*G*mC*mC*mU

ASO3 (SEQ ID NO. 15): mG*mG*mC*mC*mU*C*T*C*T*T*C*G*T*G*G*mU*mC*mC*mC*mA

ASO4 (SEQ ID NO. 16): mA*mU*mG*mC*mC*T*C*G*G*A*T*T*C*T*A*mU*mC*mC*mU*mC

ASO5 (SEQ ID NO. 17): mG*mU*mU*mG*mC*A*C*C*A*T*C*T*C*C*T*mG*mG*mC*mU*mA

ASO6 (SEQ ID NO. 18): mU*mG*mG*mU*mG*A*T*G*T*G*G*C*T*G*G*C*T*G*mU*mC*mC*mU*mG

PREVENTING TUMOR DEVELOPMENT AND METASTASIS

CROSS-REFERENCES TO RELATED APPLICATIONS

This application is a continuation-in-part application of Ser. No. 14/814,130, filed Jul. 30, 2015, which claims priority to U.S. Ser. No. 62/031,021, filed Jul. 30, 2014, each of which is incorporated by reference herein in its entirety for all purposes.

STATEMENT REGARDING FEDERALLY SPONSORED RESEARCH

Not applicable.

FIELD OF THE INVENTION

The present invention relates to novel methods to prevent tumor metastasis and suppress tumor growth, especially of solid tumors, by interfering with tumor communication and its environment and by impacting the formation and development of the tumor microenvironment.

DESCRIPTION OF RELATED ART

Tumor development occurs following the accumulation of genetic and epigenetic alterations in tumor cells. It has been demonstrated that tumor growth is strongly influenced by non-malignant cells that together with the tumor cells form the tumor microenvironment. Numerous reports have revealed the complexity of the communication between tumor cells and the heterogeneous population of stromal cells within the tumor microenvironment.

For example, the tumor-stromal cell interactions have a crucial role in tumor initiation and progression. These stromal cells, including fibroblasts, myofibroblasts, endothelial cells, mesothelial cells, adipocytes, tissue resident stem cells, and immune cells, are involved in tumor development via several mechanisms including:

(i) cell-cell and cell-matrix interactions influencing cancer cell sensitivity to apoptosis;
(ii) local release of soluble and genetically modifying factors promoting survival and tumor growth, growth of tumor blood vessels and resistance to attack by the patient's immune system (crosstalk between stromal, immune cells and tumor cells);
(iii) direct cell-cell interactions with tumor cells (crosstalk or oncologic trogocytosis);
(iv) generation of specific properties and niches within the tumor microenvironment that facilitate the acquisition of drug resistance; and
(v) conversion of cancer cells to cancer-initiating cells or cancer stem cells.

These interactions between malignant and non-malignant cells modify cellular compartments, leading to the co-evolution of tumor cells and their microenvironment.

Although the importance of microenvironmental alterations in tumor development is recognized, the molecular mechanisms underlying these changes are only now beginning to be understood. Detailed molecular characterization of various cell types from normal breast tissue, ductal carcinoma, and invasive breast tumors has revealed that gene expression changes occur in all cell types during breast tumor progression.

Recently, it has been shown that, in addition to bone marrow-derived MSCs, adipose tissue-derived MSCs display significant affinity to tumor microenvironment. The role of inflammation in the tumor microenvironment is crucial in the pathology of cancer because it regulates the directional movement of tissue resident immune cells and stem cells.

Although decades of research have yielded targeted therapies that are effective in eliminating or reducing some tumors, breast cancer remains the leading cause of morbidity and second-leading cause of death in women. Recent published reports suggest that reciprocal influences exist between breast tumor cells and the tumor microenvironment and that these interactions affect the growth and energetics of the tumor. These interactions reveal the contributions of individual cells within a tumor to the overall disease. In addition, a neurological tumor such as glioblastoma multiforme is even more malignant and the 5-year survival rate of patients diagnosed with such a tumor still is below 5%.

The present invention provides novel compositions and methods to affect the interactions between a tumor and its microenvironment to prevent, reverse, and/or reduce tumor growth and metastasis.

BRIEF SUMMARY OF THE DISCLOSURE

The present disclosure provides novel therapies for tumors, especially solid tumors, including breast cancers or glioblastomas, by interfering with tumor communication with the tumor environment and/or by regressing formation of the microenvironment, thereby preventing or reversing tumor metastasis and suppressing tumor growth. In a preferred embodiment, the present invention discloses a cancer therapy by silencing TRAF3IP2 and/or RAB27A expression.

Silencers can be delivered to a tumor in a number of ways, including at least:

1) Delivering silencing RNA by injecting an expression vector encoding the silencer to the tumor site, e.g., directly into a tumor site under visual, ultrasound, fluoroscopy, CT or MRI guidance or other imaging modalities, or indirectly through blood vessels or ducts that lead to the tumor.

2) Use of silencing RNA delivered by tumor targeting cells, such as migratory stem cells, e.g., MSCs, or any type of cells that due to their nature preferably migrate and engraft to the tumor site. Such cells would contain therein either an expression vector or a genomic copy of the sequence encoding the silencer.

3) Delivering encapsulated or otherwise protected silencing RNA to the tumor site. The silencing RNA is for example encapsulated into microspheres (i.e. exosomes) or micelles, liposomes and the like. The microspheres will be delivered by direct or indirect injection to the tumor site either trough a transcutaneous injection or through a vessel or duct supplying the tumor site. Preferably, such RNAs will be RNAse resistant, and if so, naked RNA may be used.

4) Silencing RNA linked to a specific tumor directed antibody or protamine coupled construct to increase the tumor specific concentration and to enhance the local effect of the silencing RNA within the tumor site.

5) Achieving a selective effect targeting the tumor cells and virtually avoiding an effect on non tumor cells by i) increasing the local concentration within the tumor by selective delivery means as described above, ii) by the fact that the respective genes of TRAF3IP2 and of Rab27a are ten to thirty times (respectively) upregulated in tumor, especially in tumor stem cells, compared to normal stem cells, and iii) the silencer is released in a (transactivator)-inducible manner (such as IL1B), thus expression is activated mainly in the tumor.

6) Combinations and variations of the above.

Silencing TRAF3IP2 in tumor cells confines cytokine expression and ultimately limits the development of the tumor microenvironment. This eventually slows or prevents tumor growth and restrains tumor metastasis. The tumor cells exhibit significantly higher levels of exocytosis activities compared to non-malignant cells.

Two alternative transcripts of TRAF3IP2 encoding different proteins have been identified. A third transcript, which does not encode a protein and is transcribed in the opposite orientation, has also been identified. Overexpression of this transcript has been shown to reduce expression of at least one of the protein encoding transcripts, suggesting it has a regulatory role in the expression of this gene and indicating its use in the methods described herein.

For the actual silencer sequence used in our proof of concept studies, we used commercially available silencers (SIGMA ALDRICH®) RNA to target TRAF3IP2 and RAB27A either separately or in combination. However, any type of silencer for these genes could be used.

Basic design rules for the various types of silencers are available, and once designed the silencers can be tested for efficacy according to the methods discussed herein and in the literature.

For example, a short hairpin silencer (shRNA) generally has about 18-30 nucleotides (nt), preferably 21 nt, comprising a unique sense strand of target mRNA beginning with AA linked to a loop (3-9 nt) linked to an complement of the unique sense strand and finishing with polyT, thus forming a hairpin. An initiating G nt could also be used.

Another type of silencer, is the siRNA of about 18-30 nt, preferably 21 nt, comprising a unique sense strand of the target mRNA beginning with AA and finishing with polyT.

Another type of silencer is the antisense sequence. These can be a unique antisense sequence from the target, or an RNAse resistant 18-30 nt antisense RNA sequence from the target. Effective antisense silencers may also be located in exons, but close to the acceptor splice site (SS).

miRNAs generally work when about 21-23 nt and have complementarity maintained in the first third of the small RNA and target mRNA, but mismatches arise in the remainder of the aligned sequence.

The above rules are guidelines only, however, and there is certainly variability in approaches. Therefore, it is typical to design 4-6 such silencers using the basic rules and then test each for activity, e.g., in an ex vivo system. Therefore, given the validity of the target, silencers can be readily be designed using the target sequence.

In addition, validated silencers for several genes are already commercially available. LIFE TECHNOLOGIES® for example has 27 validated silencers (6 human) for TRAF3IP2, and 9 for RAB27A (3 human). SIGMA-ALDRICH® also provides several shRNAs and siRNAs for use, including the human TRAF3IP2 silencer MISSION® shRNA Lentiviral Transduction Particles (SHCLNV-NM_147200) and the human RAB27a silencer MISSION® shRNA Lentiviral Transduction Particles (SHCLNV-NM_004580). In addition, Sigma offers miRNA mimics, and esiRNA. Furthermore, the RNAi Consortium has built a library of shRNAs directed against 15,000 human and 15,000 mouse genes.

Furthermore, silencer RNAs can be stabilized against nucleases by incorporating modified bases therein, such as methylphosphonate, phosphorothioate, α-nucleoside, 2'-O-substituted RNA, phosphoramidite, morpholino and chimeras contain an internal core of unmodified phosphodiester RNA/RNA flanked by modified residues. These can be very useful where naked or encapsulated nucleic acid is directly delivered, as opposed to an expression vector encoding the silencer.

We have specifically targeted breast cancer and glioblastoma cell lines herein for proof of concept experiments, but we anticipate that the method can be used in many cancers or inflammatory conditions since TRAF3IP2 and/or RAB27A play a role therein. The TRAF3IP2 gene, for example, is implicated in several cancers, including but not limited to lung cancer, colon cancer, cervical cancer, endometrial cancer, liver cancer, ovarian cancer, prostate cancer, gastrointestinal cancer, testis cancer, thyroid cancer, carcinoid tissue, urothelial cancer, pancreatic cancer, sarcomas, melanoma and the like. See e.g., proteinatlas.org/ENSG00000056972-TRAF3IP2/cancer. It is also implicated in inflammatory bowel disease, atopic dermatitis, psoriasis, Hodgkins disease, familial candidiasis, possibly ulcerative colitis, and the like. Any cancer or diseased tissue with at least 5 or 10 fold or higher levels of either of these transcripts can be addressed by in the methods herein.

RAB27A mainly regulates exocytosis, and thus silencing RAB27A attenuates exocytosis. The lower exocytosis limits the release of oncogenic molecules into the tumor microenvironment in both soluble and insoluble forms. This ultimately restricts the development of tumor microenvironment.

RAB27a is known to be highly expressed in some cancer as well, including pancreatic cancer, breast cancer, colorectal, lymphoma, prostate, melanoma, ovarian, thyroid, and the like.

While there are several methods of delivering silencers to tumors, one preferred method uses of mesenchymal stem cells or "MSCs". Using their known preferred tumor homing capacity, MSCs are modified with a vector expressing the respective silencing sequence. Silencing vectors are thus delivered to the tumor site foci using these MSCs that produce the respective silencing RNA against TRAF3IP2, Rab27a, or against both. In addition and as a means to increase the effect on tumor cells and minimize the effect on non-tumor cells, tumor-tropic subset of MSCs that are obtained and identified by their preference to migrate towards the tumor cells can be used. They can be created by prior exposure to exosomes that induce the needed epigenetic changes in the MSC or by selecting by FACS sorting MSCs expressing specific tumor surface markers, such CXCR4, or the PDGF bb receptor.

The tumor-tropic MSCs carrying therapeutic vectors will home to the vicinity of tumor cells and then express the silencers in the tumor microenvironment where there is higher expression of IL1B, if we use an IL1B inducible promoter herein. The silencer is thus released and reduces tumor-related inflammation and tumor size with minimal off-target effects since healthy tissue won't have high levels of IL1B. The MSCs containing silencing vector ($5 \times 10^5$/subject) are administered systemically, e.g., by injection into the bloodstream, into a local tumor supporting blood vessel or duct, or directly transcutaneous into the primary tumor or its metastasis.

Although we have used MSCs as delivery vehicles herein, this is an continually evolving area of research and another method may ultimately emerge as more preferred over the course of research. Other possible delivery vehicles include Rexin-G, an engineered retroviral nanoparticle that achieves targeting to cancerous lesions through the attachment of a collagen motif that binds to "newly exposed" extracellular matrix, which is typically associated with tumor tissue. Another possibility is to use a virus engineered to target a particular cancer cell, such as the parvo virus H1, or to link the silencer with tumor specific ligand or antibody.

There are also non-viral methods of silencer delivery, including e.g, injecting naked DNA/RNA into a tumor, injected protected RNA into tumors, electrotransfection, the use of polymers, liposomes, and the like, to protect the nucleic acids, or to stabilize the silencer through linking it to Protamin.

Lentiviral vectors were used herein to encode the silencer sequences for TRAF3IP2 and RAB27A. Although data show that there is specificity for CD45+ cells transduction in vivo when administering lentiviral vectors, MDA-MB231 and SW620 cells are highly transducible with lentiviral vectors. Thus, these vectors were useful for proof of concept studies. However, any suitable expression vector may be used herein, or the gene can be introduced into the genome of a homing cell (e.g., by homologous recombination), such as the MSCs discussed herein.

Common vectors are based on herpes simplex type 1 recombinant vector (HSV-1); adenovirus, adeno-associated viral vector (AAV); alpha virus; vaccinia virus; pox virus; sendai virus; plasmids; retrovirus; ssDNA vectors; and the like. To date, adenovirus, retrovirus and naked plasmid DNA have made up more than half of the vectors tested in clinical trials of various gene therapies.

An IL1B transactivator-inducible system is a preferred promoter for use in our lentiviral vector. The IL1B promoter activates the expression of silencer RNA by binding the endogenous IL1B, which is highly produced by cells within tumor microenvironment. However, this promoter is exemplary only and there are many to choose from, including several antibiotic resistance or drug responsive promoters that can be safely used in humans (e.g., tamoxifen, tetracyclin, ampicillin and the like).

The disclosure provides one or more of the following embodiments, in any combinations(s) thereof:

A pharmaceutical composition for the treatment of a tumor having increased expression of TRAF3IP2, wherein said composition comprises at least one silencing sequence for TRAF3IP2 in a pharmaceutically acceptable carrier in an amount effective for the therapeutic treatment of a tumor, wherein said silencing sequence reduces the expression of the TRAF3IP2 gene by at least two-fold as comparing to without the silencing sequence for TRAF3IP2, and wherein said silencing sequence is a modified portion of sense strand of NM_001164281.2 (SEQ ID NO. 7), NM_147200.2 (SEQ ID NO. 8), XM_011535386.2 (SEQ ID NO. 9), NM_147686.3 (SEQ ID NO. 10), XM006715319.4 (SEQ ID NO. 11), and NM_001164283.2. (SEQ ID NO. 12).
Any composition herein described, the composition comprises an expression vector encoding a TRAF3IP2 silencer operably coupled to an inducible promoter.
Any composition herein described, the silencing sequence is an siRNA, an miRNA, an shRNA, an antisense RNA, or an antisense oligonucleotide.
Any composition herein described, the silencing sequence encoded by an expression vector hosted in a mesenchymal stem cell (MSC) that targets said tumor.
Any composition herein described, the MSC having been previously exposed to exosonnes from said tumor.
Any composition herein described, the silencing sequence is an antisense oligonucleotide that is 13-25 nucleotides in length
Any composition herein described, wherein said silencer is an siRNA, an shRNA, an miRNA, or an antisense oligonucleotide.
Any composition herein described, wherein said silencer comprises any sequence herein referenced or described.
Any composition herein described, the antisense oligonucleotide is complementary to a portion of the sense strand of any one of SEQ ID NOs. 7-12.
Any composition herein described, the antisense oligonucleotide is selected from SEQ ID NOs. 13-18.
Any composition herein described, the pharmaceutically acceptable carrier is a nucleic acid carrier.
Any composition herein described, further comprising a silencing sequence for Rab27a.
Any composition herein described, the composition is formulated for parenteral administration, including direct injection into a tumor or its metastasis site by transcutaneous, intraarterial, intraductal, intradermal, intramuscular, intraperitoneal, or subcutaneous administration.
Any composition herein described, the composition is used in treating glioblastoma or breast cancer, or for use in treating any cancer with at least 2-fold increased TRAF3IP2 and/orRab27a expression
A method of treating at least one tumor in a mammal comprising administering to the mammal an effective amount of any composition herein.
A method as herein described, wherein said tumor is a human breast cancer or a glioblastoma or any cancer with at least 2-fold increased TRAF3IP2 and/or RAB27A levels, or at least 10 fold, or at least 20 fold or at least 30 fold.
A method as herein described, wherein the composition is injected directly into said tumor and said injection is guided by ultrasound, fluoroscopy, imaging, CT, MRI, or just visually in order to enhance the local concentration of the silencer within the tumor.
A method as herein described, wherein the silencers are delivered to the tumor by an expression vector.
A method as herein described, wherein said silencers are encoded by expression vectors contained inside MSCs.
A method as herein described, wherein the silencers are delivered to the tumor by injection.
A method as herein described, wherein the silencers linked to an antibody targeting a breast tumor specific cell surface antigen.
A method to selectively treat a tumor and minimize side effects, by administering an effective amount of a silencer for TRAF3IP2 or Rab27a, or both, to a tumor that expresses at least 2 times the amount of TRAF3IP2 or Rab27a, or both, as compared to a non-tumor cell from the same tissue.

| -continued |
|---|
| A method as herein described, further comprising enhancing the selective effect on tumor cells and avoiding effects on normal cells by increasing the local concentration of the silencer within the tumor by injecting said silencer(s) directly into said tumor. |
| A method as herein described, wherein said silencer(s) is encoded in an expression vector having an inducible promoter, thus enhancing the selective effect on tumor cells and avoiding effects on normal cells by means of selectively activating the production of the silencer by a switch that activates said inducible promoter. |
| A method as herein described, wherein said switch is preferentially or only found in said tumor. |

As used herein, the term "expression vector" means a DNA or RNA into which a sequence of interest can be inserted that operably linked to a promoter such that the sequence will be transcribed or expressed from the promoter in the host cell/animal of interest. Thousands of such vectors are available. See e.g., Addgene.org which provides both a repository and a searchable database allowing vectors to be easily located and obtained from colleagues. See also Plasmid Information Database (PlasmID) and DNASU having over 191,000 plasmids. A collection of cloning vectors is also kept at the National Institute of Genetics as a resource for the biological research community. Furthermore, vectors (including particular ORFS therein) are usually available from colleagues.

As used herein, the term "silencing" refers to the down-regulation of gene expression. At least 65%, 70%, 75%, 80% reduction should be achieved, but preferably, this term refers to the ability of a cell to prevent the expression of a certain gene. Gene silencing can occur during either transcription or translation and is often used in research and gene therapies.

By "preventing" gene expression, we mean no detectable intact gene expression is detected when assayed by Northern blot using a radioactively end-labeled oligomer that is complementary to the gene being silenced. Nonetheless, there may be minute amounts of expression that could be detected by extremely sensitive methods.

The term "silencer" as used herein refers to a exogenous sequence that can be introduced into cells and used to silence gene expression in that cell. There are several different types of silencers, including at least antisense oligonucleotides, ribozymes, RNA interference, and the like. Genes can be silenced by e.g., dsRNA that decomposes mRNA, siRNA molecules that cause the endonucleatic cleavage of the target mRNA molecules or by miRNA molecules that suppress translation of the mRNA molecule or by shRNA, as well as by endoribonuclease-prepared siRNAs (esiRNAs), which are a mixture of siRNA oligos resulting from cleavage of long double-stranded RNA (dsRNA) with an endoribonuclease such as *Escherichia coli* RNase III or dicer. The term "silencer" is not limited to any one particular methodology, unless so specified.

By "exosomes" what is meant herein are cell-derived vesicles that are present in many and perhaps all biological fluids, including blood, urine, and cultured medium of cell cultures.

As used herein, the expressions "cell", "cell line" and "cell culture" are used interchangeably and all such designations include progeny. Thus, the words "cells" and similar designations include the primary subject cell and cultures derived therefrom without regard for the number of transfers. It is also understood that all progeny may not be precisely identical in DNA content, due to deliberate or inadvertent mutations that arise after genetic engineering is concluded. Mutant progeny that have the same function or biological activity as screened for in the originally transformed cell are included. Where distinct designations are intended, it will be clear from the context.

The terms "operably associated" or "operably linked," as used herein, refer to functionally coupled nucleic acid sequences.

As used herein "recombinant" is relating to, derived from, or containing genetically "engineered" material. In other words, the genome was intentionally manipulated by the hand of man in some way.

"Reduced activity" or "inactivation" is defined herein to be at least a 75% reduction in protein/gene activity, as compared with an appropriate control species. Preferably, at least 80, 85, 90, 95% reduction in activity is attained, and in the most preferred embodiment, the activity is eliminated (100%). Proteins can be inactivated with inhibitors, by mutation, or by suppression of expression or translation, and the like. A negative superscript, as in ACT F, indicates reduced activity.

As used herein, "pharmaceutically acceptable carrier" refers to any carrier that is capable of delivering oligonucleotide to target cells. Examples of the pharmaceutically acceptable carrier include, but not limited to, nucleic acid carrier, cationic lipids, peptide-mediated carrier such as cell-penetrating peptides, nanogel carrier, liposomes, small molecule tags (including cholesterol-modification, membrane-permeant peptides, folate, antibiotics, VITE, and VITA), and cationic polymers.

As used herein the specification, "a" or "an" may mean one or more. As used herein in the claim(s), when used in conjunction with the word "comprising", the words "a" or "an" may mean one or more than one. As used herein "another" may mean at least a second or more.

The term "about" means the stated value plus or minus the margin of error of measurement or plus or minus 10% if no method of measurement is indicated.

The use of the term "or" in the claims is used to mean "and/or" unless explicitly indicated to refer to alternatives only or if the alternatives are mutually exclusive.

The terms "comprise", "have", "include" and "contain" (and their variants) are open-ended linking verbs and allow the addition of other elements when used in a claim.

Wherever any of the phrases "for example," "such as," "including" and the like are used herein, the phrase "and without limitation" is understood to follow unless explicitly stated otherwise. Similarly "an example," "exemplary" and the like are understood to be non-limiting.

The term "substantially" allows for deviations from the descriptor that do not negatively impact the intended purpose. Descriptive terms are understood to be modified by the term "substantially" even if the word "substantially" is not explicitly recited. Therefore, for example, the phrase "wherein the lever extends vertically" means "wherein the lever extends substantially vertically" so long as a precise vertical arrangement is not necessary for the lever to perform its function.

The disclosure may use one or more of the following abbreviations:

| Abbreviation | Meaning |
| --- | --- |
| ASO | Anti-sense Oligonucleotides |
| ASC | Adipose tissue derived stem cells |
| bi-shRNA | bifunctional shRNA |
| esiRNA | Endoribonuclease-prepared siRNAs |
| GFP | Green fluorescent protein |
| KD | Knock down (refers to silencers herein) |
| miRNA | nnicroRNA |
| MSC | Mesenchymal stem cells |
| RAB27A | RAS-ASSOCIATED PROTEIN 27A (UniProt P51159) |
| RFP | Red fluorescent protein |
| RNAi | RNA interference |
| shRNA | Small hairpin RNA |
| siRNA | Small interfering RNAs |
| TRAF3IP2 | TRAF3-INTERACTING PROTEIN 2 aka NUCLEAR FACTOR KAPPA-B ACTIVATOR 1 or ACT1 (UniProt O43734) |

BRIEF DESCRIPTION OF THE DRAWINGS

FIG. 3A shows intra-mammary engraftment of MSCs. The MSCs were exposed to purified $MDA_{Exo}$ for 14 hours and then $5 \times 10^5$ cells (in Martigel) were engrafted into mammary glands of NIHIII nude mice (female, 6-8 weeks old). The animals were observed for tumor growth weekly and euthanized after 12 weeks. Panels (from left to right) show the animals injected with PBS, Martigel, and unexposed MSCs as controls. The MSC-exposed animals develop tumors at the site of injection versus no visible tumors growing on the controls. The euthanized animals were dissected at week 12 post-engraftment. Histology on the tumor tissue show positive immuno-reaction to pencytokeratin E-cadherin antibodies (Leica, 20×).

FIG. 3B shows methylation levels increased in exposed MSCs. MSCs exposed to MDA-MB-231 culture condition media and $MDA_{Exo}$ show enhanced levels of methylation; the methylation levels are reversible when exposed MSCs are treated with 5-Aza-2'-deoxycytidine (n=5, P<0.05).

FIG. 3C shows methylated genes in MSCs. Using PCR array, the methylated genes were identified in MSCs exposed to MDA-MB-231 culture condition media and $MDA_{Exo}$ (n=3, p<0.05).

FIG. 4A shows the expression of TRAF3IP2 and RAB27A in cultures of MDA-MB231, 184A1 and MSCs. The expression of both TRA3IP2 and RAB27A are significantly higher in MDA-MB231 cells than in 184A1 and MSC cells. The co-cultures of 184A1 and MSCs with MDA-MB231 cells enhanced the expression of TRAF3IP2 and RAB27A in both 184A1 and MSCs.

FIG. 4B Using silencing RNA, the expression of TRAF3IP2 and RAB27A were silenced in MDA-MB231, 184A1 and MSCs. The doubling time was calculated and compared to wild type cells. The silencing of RAB27A and TRAF3IP2 decreases the proliferation of MDA-MB231 cells, while having no effect on MSC replication capacity.

FIG. 4C Using a protein array technique, the cytokines released in culture media (CM) of MDA-MB231 and $MDA_{KDTRAF3IP2}$ cells were assessed. Cytokine array analysis shows that the level of cytokines mostly involved in breast cancer progression and metastasis are significantly reduced in $MDA_{KDTRAF3IP2}$ cells (n=3; P<0.05).

FIG. 8 shows the sequence of several silencer sequences, or provides an accession number for same.

FIG. 17B. Antisense oligonucleotide design for TRAF3IP2 silencing.

DETAILED DESCRIPTION OF THE DISCLOSURE

Figure 1:
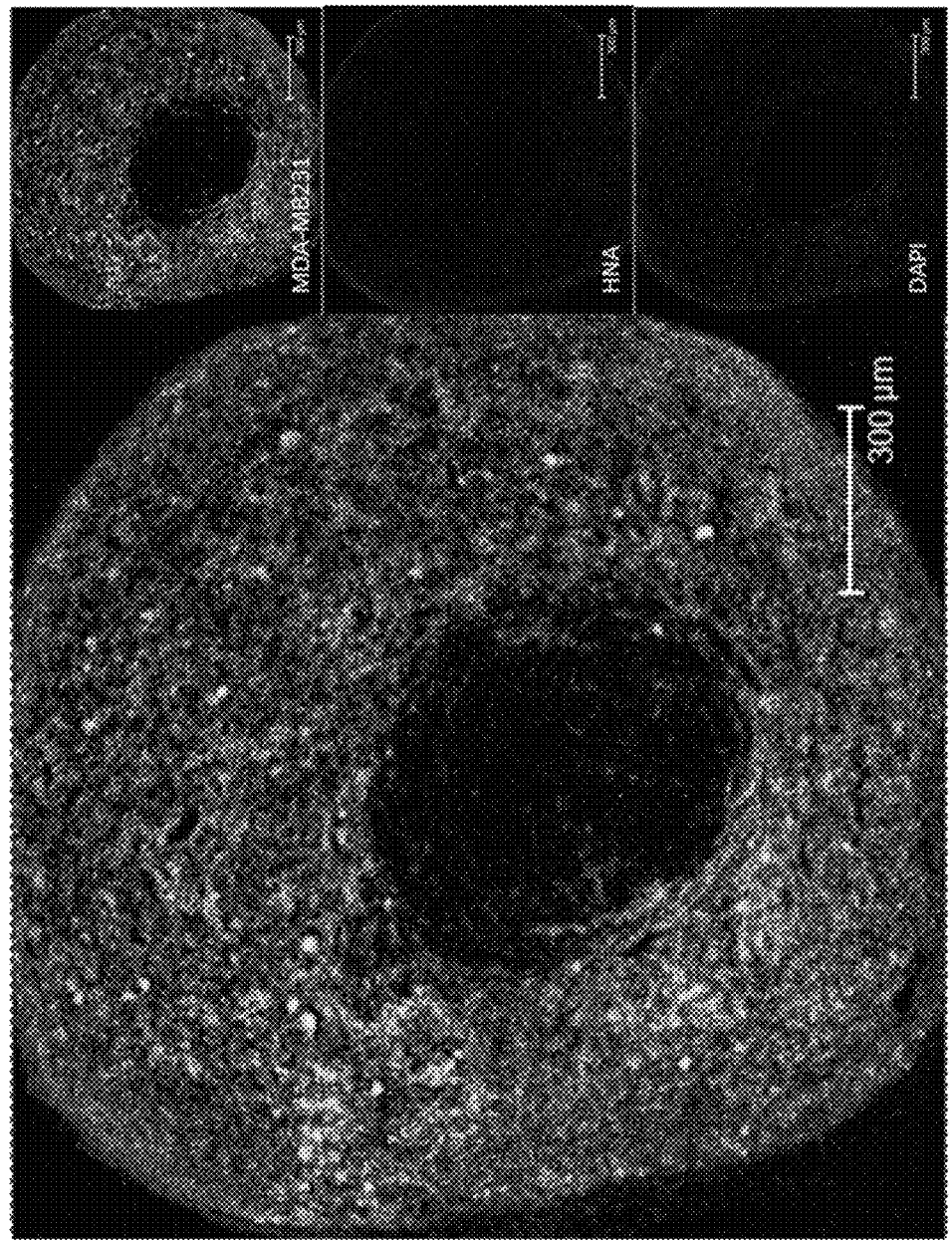
FIG. 1 shows the localization of MSCs in tumor location. MDA-MB231 of genetically modified GFP expressing cells were injected intra mammary in 4-6 week old NIHIII immune-deficient female mice (n=5). $5 \times 10^5$ MSC cells were injected into the tail vein of these animals, which were euthanized 7 weeks post injection. The tumor tissues were extracted, fixed, and subjected to immunohistochemistry using HLA antibody to detect the human cells and DAPI for staining DNA. The samples were imaged with Leica confocal microscope (10×).
Figure 2:
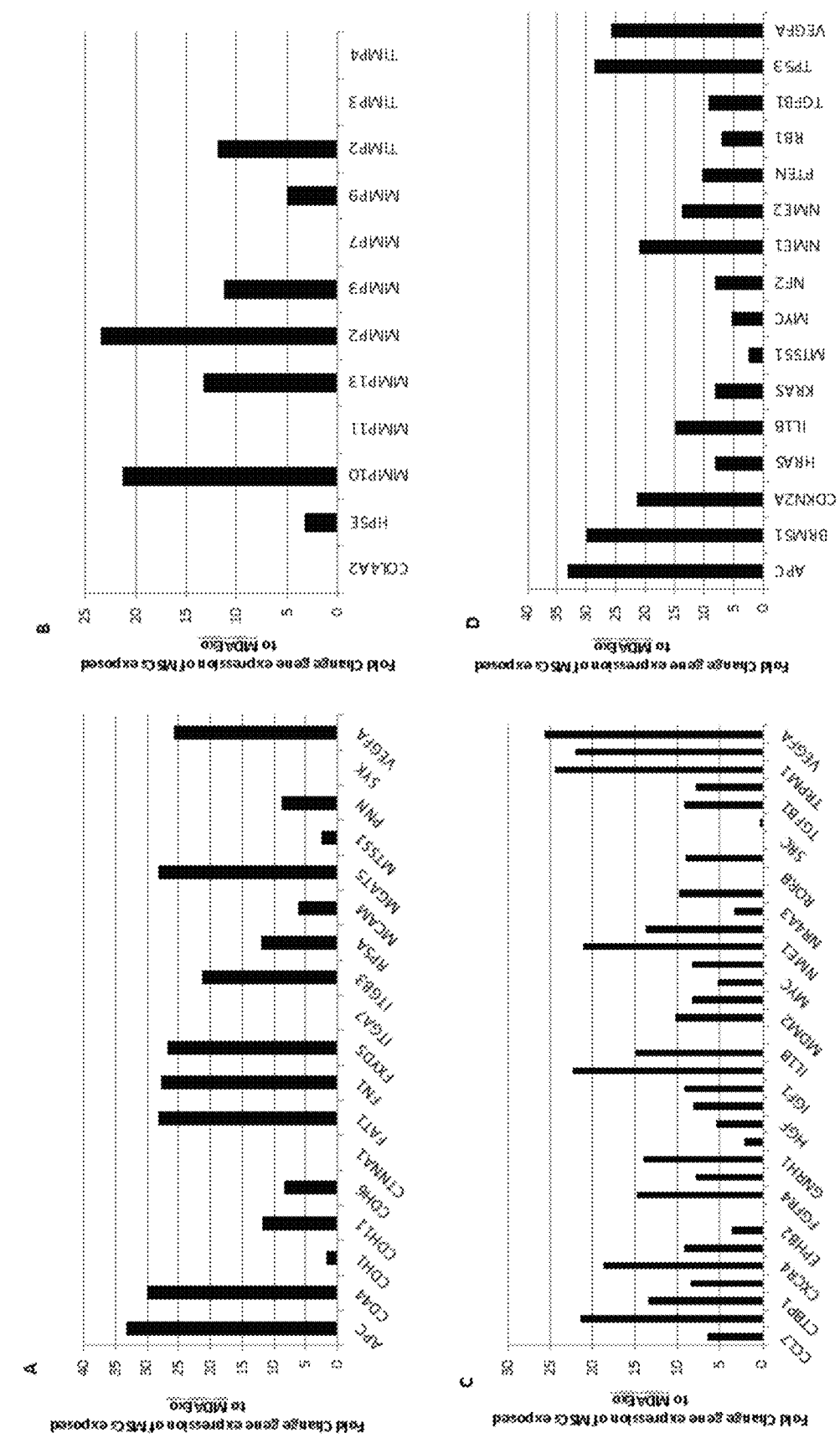
FIG. 2 shows the effect of exosomes on the gene expression of MSCs. To study the effect of exosomes on MSCs' gene expression, MSCs were incubated with purified exosomes derived from MDA-MB231 cells ($MDA_{Exo}$) for 14 h in 37° C. and 5% $CO_2$. The changes in gene expression in MSCs were assessed using PCR array. The perturbed genes that displayed greater than two fold changed expression were grouped based on their function of cell adhesion (A), extracellular matrix proteins (B), cell growth and proliferation (C), and cell cycle (D). The graphs are representatives of triplicate experiments (P<0.05).

Detailed descriptions of one or more preferred embodiments are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in any appropriate manner.

Furthermore, while the invention is exemplified in breast cancer cell lines injected into mice with particular vectors and silencers, this is for proof of concept only, and the methods are expected to work in many different tumors with a variety of silencer delivery methods and with a variety of silencer sequences.

The following materials were used herein:

| | |
|---|---|
| MDA-MB231 cells | A human breast cancer cell line, available from Sigm-Aldrich ® |
| MDA$_{KDTRAF3IP2}$ cells | MDA-MB231 cells transformed with a lentiviral vector encoding a TRAF3IP2 silencer. |
| MDA$_{KDRab27}$ cells | MDA-MB231 cells transformed with a lentiviral vector encoding RAB27A silencer |
| 184A1 cells | A human mammary gland cell lines, established by chemical transformation (ATCC ® CRL-8798) |
| Lentiviral vector | A lentiviral-based vector (e.g. pLKO.1-puro or pLKO.1-puro-CMV-TurboGFP-™), preferably having a transactivator inducible promoter, such as IL1B promoter which will be activated in presence of excessive amounts of IL1B within tumor microenvironment. |
| U87 | U87 is a human primary glioblastoma cell line formally known as U-87 MG. It has epithelial morphology, and was obtained from a stage four 44 year-old cancer patient, and can be obtained from ATCC (HTB-14). |
| SVg12 | SVg12 is scrambled silencer RNA construct in a lentiviral vector that functions as a control for transduction in these experiments. |

Exosomes

Exosomes are the main insoluble components of the tumor microenvironment. Exosomes are small membranous extracellular vesicles (40-140 nm in diameter) that are released in extracellular space. In addition to production by tumor cells, exosome-like vesicles are produced by various non-malignant cell types. Structurally, these vesicles consist of a lipid bi-layer membrane similar to the cellular membrane, proteins, including host specific proteins, mRNA, microRNA (miRNA) and transcription factors.

Exosomes can affect various cell types by transferring their content to various cells. The growing interest in the characterization of exosome-like vesicles in cancer research arises from their potential role in carrying a large array of oncogenic elements released by malignant cells, such as oncogenic proteins and miRNAs. Such oncogenic proteins and miRNAs can traverse the tumor microenvironment and can be taken up by recipient non-malignant cells; this can result in the transfer of oncogenic activity.

It has been shown that the release of exosomes into extracellular spaces is through exocytosis. RAB27A is one of the exocytosis regulators. RAB27A, a membrane-bound protein, is thought to be important for directing secretory lysosomes to the immunologic synapse and for their release from microtubules. At the membrane, RAB27A is activated by exchange of bound nucleotide GDP for GTP. Active RAB-GTP then recruits effector proteins from the cytosol to the membrane. These are a diverse group of proteins that include lipid kinases and phosphatases, molecular motors, and tethering factors, which are involved in protein transport and small GTPase mediated signal transduction.

A tumor can neither grow nor metastasize without the development of supporting stroma. In solid tumors, the associated stroma consists of a mixture of several cell types, cytokines, chemokines, and extracellular exosome-like vesicles. These accumulations change the function and composition of tissue surrounding the cancer cells and form the tumor microenvironment. As noted above, the tumor microenvironment contains both cellular and acellular fractions. The acellular fraction, consisting mainly of soluble inflammatory cytokines and insoluble extracellular exosomes-like vesicles, is involved in tumor-related inflammation and growth. Tumor cells take part in releasing both cytokines and exosomes into the tumor microenvironment via exocytosis. Exocytosis is a cellular process that directs the contents of secretory vesicles out of the cell membrane and into the extracellular space. This process is regulated mainly by the function of the RAB27A gene.

Mesenchymal stem cells (MSCs) are a type of stromal cells abundant in the tumor microenvironment. MSCs have been identified in several tissues. Adipose tissue and bone marrow have been described among the major sources of MSCs in adults. MSCs resemble fibroblasts in terms of shape and markers; they are capable of self-renewal and contribute to tissue regeneration by differentiation into osteoblasts, chondrocytes, adipocytes, myocytes, macrophage-like cells and myofibroblasts, depending upon the requirements of the site to which they are recruited.

MSCs have been found to be incorporated into tumors as well as in inflammatory milieu, such as healing wounds. In tumor biology, the homing of MSCs to tumors is the most significant hallmarks of these cells. Several reports have indicated that MSCs are capable of homing to the tumor site, but results of current studies investigating the signals that recruit MSCs to developing tumor sites are controversial. During the normal homing process, which is common to both hematopoietic stem cells (HSCs) and MSCs, the cells migrate from their locations via proteolysis and are directed to a particular injury site. Reports indicate that MSCs are recruited to tumor sites in the same fashion. This tropism of MSCs has been exploited for gene therapy and delivering drugs in a targeted way to the tumor site, and we have also used this tropism herein.

A recently published report described the effect cytokines exert in recruitment of MSCs to the tumor site in breast cancer (Muehlberg et al. 2009, Gehmert et al. 2010, Senst et al. 2013, Ilmer et al. 2014). It also showed that co-culturing MSCs and MDA-MB231 cells (MSC+MDA-MB231) enhances the expression of cytokines from tumor cells. GRO-α, IL6, IL8, CXCL1 and MCP1 are chemoattractant proteins. As these chemoattractants are released at a high level when MSCs and cancer cells are in proximity they have a significant effect in MSC homing towards tumor cells (Id.).

To study the homing capability of MSCs into a tumor site in vivo, genetically modified GFP-expressing MDA-MB231 cells were injected intra-mammary into 4-6 weeks old NIHIII immune-deficient female mice (n=5). $5 \times 10^5$ MSCs were injected into the tail vein of these animals. The tumor tissues were extracted seven days following MSCs injections, and the tumor tissue was harvested, fixed, and subjected to immunohistochemistry using HNA antibody to detect the human cells and DAPI for staining DNA.

FIG. 1 shows the homing of MSCs in tumor site. These experiments confirm that MSCs are highly suitable to be used as delivery agents to deliver silencers to the tumor site as they preferably engraft to the tumor because they are attracted by respective cytokines produced and released by the tumor cells.

MSC Effect on Tumors

MSCs contribute to tumor growth in a number of ways, including their roles in expressing growth factors and enhancing vessel formation. Data has shown that the tumor microenvironment modifies MSCs' properties toward promoting breast cancer and metastasis, especially for MSCs residing in breast adipose tissue, called adipose derived stem cells or "ASCs".

To study the effect of insoluble factors on stromal cells, including MSCs, exosomes were purified from cultures of MDA-MB231 cells. MSCs were incubated with purified exosomes from MDA-MB231 cells ($MDA_{Exo}$) for 14 hours in 37° C. and 5% $CO_2$. The changes in the gene expression in MSCs were assessed, and the graphs illustrated in FIG. 2A-2D shows the genes modified following MSCs exposure to $MDA_{Exo}$.

The exosome exposed MSCs ($5 \times 10^5$) are called $MDA_{Exo}$ herein and were injected intra-mammary into NIHIII immune-deficient mice. The animals developed a growing tumor-like mass at the site of injection within 12 weeks, as shown in FIG. 3A. Exposure to either MDA-MB231 culture condition media or to $MDA_{Exo}$ enhances the methylation in MSCs, as seen in FIG. 3B. The methylation level was reversible when $MDA_{Exo}$-exposed MSCs were treated with 5-Aza-2'-deoxycytidine. The gene expression analysis showed several genes, including BRCA1, PAX5, and APC, were highly methylated, as shown by FIG. 3C.

Silencing TRAF3IP2 and/or RAB27A

Tumor microenvironment components that are initially released from breast cancer cells activate the key transcription factors in inflammatory and stromal cells, similar to those described in breast cancer cells. This leads to the production and release of inflammatory mediators, which proceed to trigger cancer-related inflammation. The IKK/NF-κB signaling pathway has been shown to transcriptionally regulate inflammatory cytokine expression, and both IKK and NF-κB have been targeted to reduce cancer-related inflammation in the tumor microenvironment. However, these approaches were unsuccessful due to the activation of alternative pathways such as Toll-like receptors (TLRs).

Figure 16:
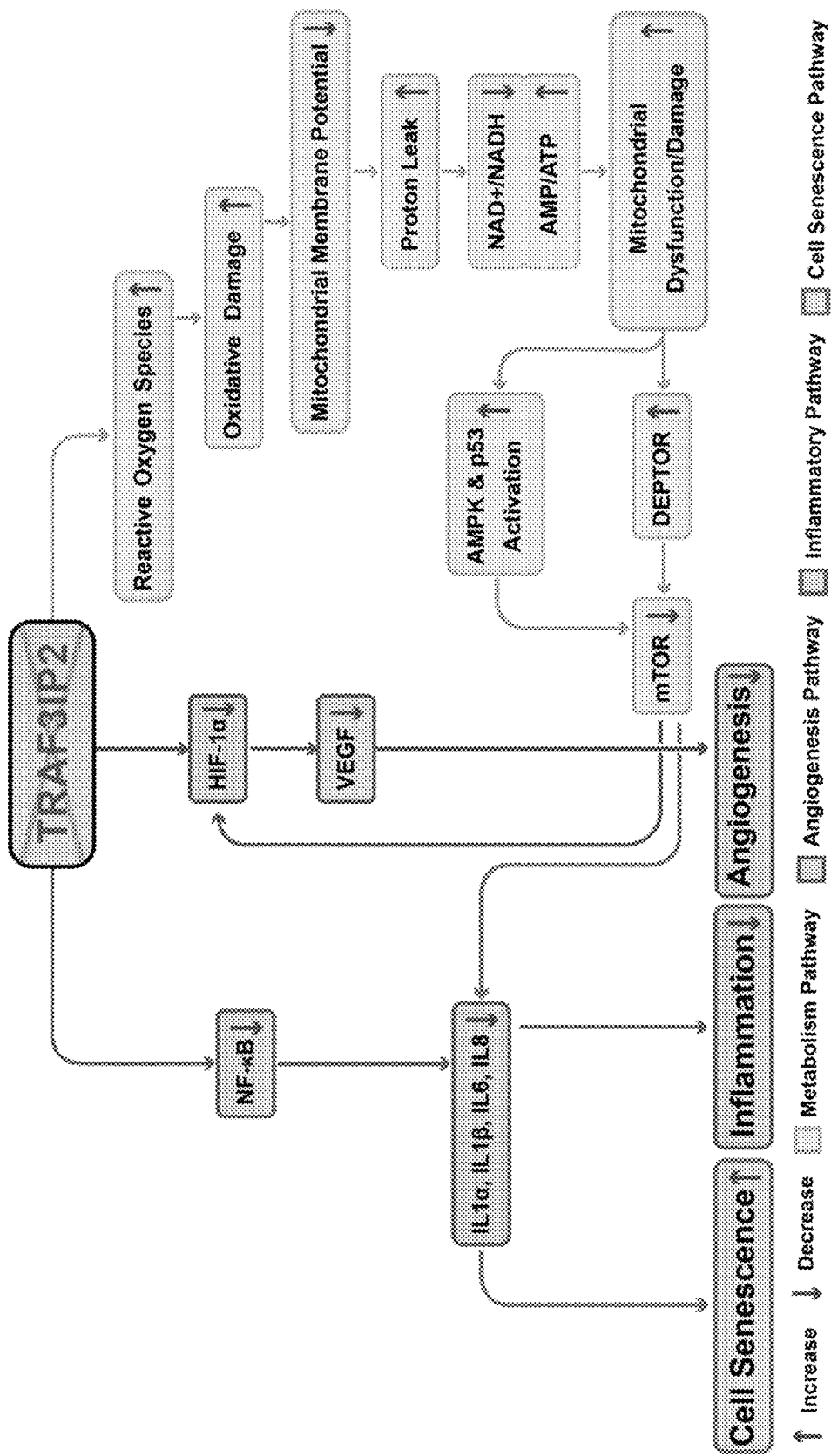
FIG. 16. Pathways involving TRAF3IP2.

TRAF3IP2 encodes ACT1, a signaling adaptor involved in the regulation of adaptive immunity. Other possible pathways involving TRAF3IP2 are shown in FIG. 16. Studies of TRAF3IP2-deficient mice suggest that TRAF3IP2 is a negative regulator of humoral immunity through its inhibitory effect on CD40- and BAFFR-mediated signaling. TRAF3IP2 operates as a positive signaling adaptor in IL-17-mediated cellular immune responses. IL-17 is a dominant 'signature' cytokine of TH-17 cells and up-regulates neutrophil-mobilizing cytokines, chemokines, and tissue-degrading matrix metalloproteases.

IL-17-dependent receptor ligation induces TRAF3IP2 recruitment to the cytoplasmic tail of the IL-17R. This in turn allows the incorporation of the TNF receptor-associated factors TRAF3 and TRAF6 into the signaling complex and the subsequent downstream activation of the MAPK and NF-κB pathway. Accordingly, TRAF3IP2 is not only involved in pathways balancing humoral and cellular immunity, but also represents a chief link between IL-17-mediated adaptive immune responses and NF-κB as the master regulator of innate immunity controlling the inducible transcription of various pro-inflammatory cytokines.

The data presented herein indicates that TRAF3IP2 mediates IKK dependent NF-κB activation as well as TLR4 signaling. It has been shown that IL-17 signals exclusively via TRAF3IP2, and TRAF3IP2 gene deletion abrogates IL-17-dependent inflammatory signaling. The novel findings of the present disclosure show a significantly high expression of TRAF3IP2 in breast cancer cells while this expression is minimal in non-malignant breast epithelial cells and MSCs.

Interestingly, the data presented here also show that the expression of RAB27A is also significantly higher in breast cancer cells compared to 184A1 cells, a non-malignant breast epithelial cell line, and MSCs, as shown in FIG. 4A. The silencing of RAB27A and TRAF3IP2 decrease the cell proliferation in MDA-MB231 cells, while the silencing of these genes has no effect on MSC replication capacity, as seen in FIG. 4B.

Silencing TRAF3IP2 in MDA-MB231 cells ($MDA_{KDTRAF3IP2}$) results in remarkable changes in expression of cytokines. Cytokine array analysis shows that the level of cytokines mostly involved in breast cancer progression and metastasis are significantly reduced in $MDA_{KDTRAF3IP2}$ cells, as shown in FIG. 4C.

Silencing TRAF3IP2 results in significant changes in the expression of factors involved in the formation of tumor microenvironment and associated inflammation. The tumor microenvironment is under constant chronic inflammatory pressure. It has been shown that one of the potent regulators of inflammation is TGF-β which was found to regulate the expression of angiopoietin-like 4 (ANGPTL4) via a Smad3-signaling pathway. The up-regulation of ANGPTL4 in cancer cells when they extravasate into the circulatory system likely explains their inclination toward colonizing lung tissue. The rationale for this is based on the ability of ANGPTL4 to disrupt the integrity of vascular tight junctions, thereby increasing the permeability of the capillaries in the lung to promote the intravasation into the lung tissue.

Figure 5:
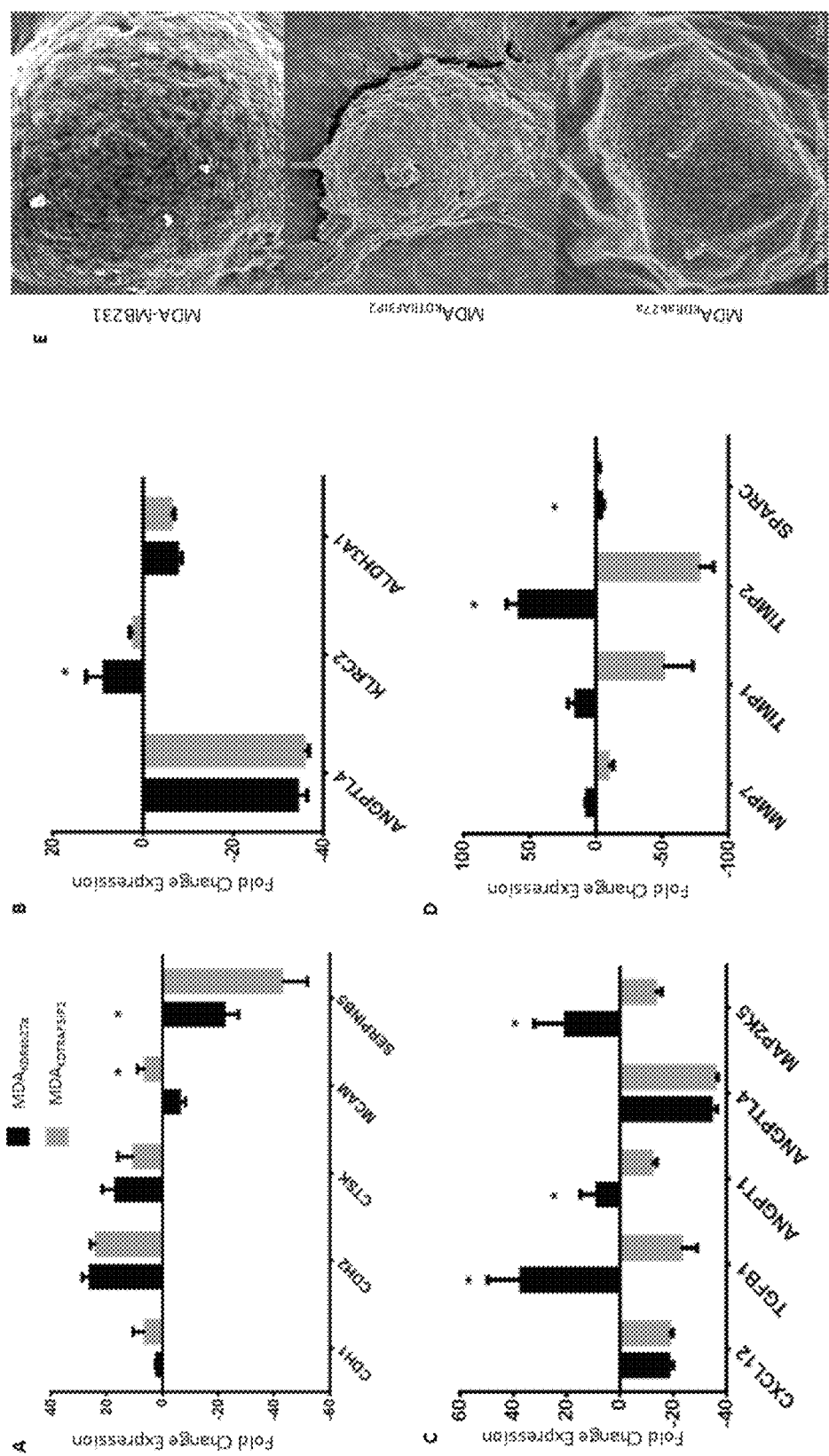
FIG. 5 shows the effect of silencing TRAF3IP2 and RAB27A on tumor cells. MDA-MB231 cells were silenced for the expression of TRAF3IP2 and RAB27A, then the selected gene expression was assessed using PCR array and compared to wild type cells set as zero in the graphs. The perturbed genes that displayed greater than two fold changed expression were grouped based on their function of cell adhesion (A), transcription factors (B), cell growth and proliferation (C), and extracellular matrix proteins (D). The graphs are representatives of triplicate experiments (P<0.05, *P<0.001). Panel (E) shows an electron micrograph of MDA-MB231, $MDA_{KDTRAF3IP2}$, and $MDA_{KDRAB27A}$ cells. The cells were negatively stained using uranyl acetate and viewed by electron microscopy. The scale bar represents 200 nm.

The present data shows a significant reduction in ANGPTL4 expression in both $MDA_{KDRab27}$ and $MDA_{KDTRAF3IP2}$, as seen in FIG. 5B. The expression of ANGPT1, which binds to extracellular matrix from carcinoma cells, is exclusively decreased in $MDA_{KDTRAF3IP2}$, while its expression is enhanced in $MDA_{KDRab27}$ cells, as shown by FIG. 5A-5D. This is due to the halt in exocytosis in $MDA_{KDRab27}$ cells. Electron microscopy indicates abnormal morphology in both $MDA_{KDRab27}$ and $MDA_{KDTRAF3IP2}$ cells.

Silencing In Vivo

The data presented above strongly suggests that silencing TRAF3IP2 and RAB27A could have potent effects in vivo, and thus, the next step was to deliver silencers to tumor cell using cancer cells that already contained the silencers.

In these experiments, the expression of TRAF3IP2 and RAB27A were silenced in MDA-MB231 cells using lentiviral-based vectors encoding silencer RNA. Female 4-6 weeks old NIHIII mice were injected intra-mammary with $1\times10^5$ $MDA_{KDTRAF3IP2}$ cells in PBS and Martigel. Another group of animals were injected with $1\times10^5$ $MDA_{KDRAB27A}$ cells in PBS and Martigel. As controls, a group of animals were injected with just $1\times10^5$ MDA-MB231 cells in PBS and Martigel, another group was injected with Martigel, and another group was injected with PBS.

Figure 6:
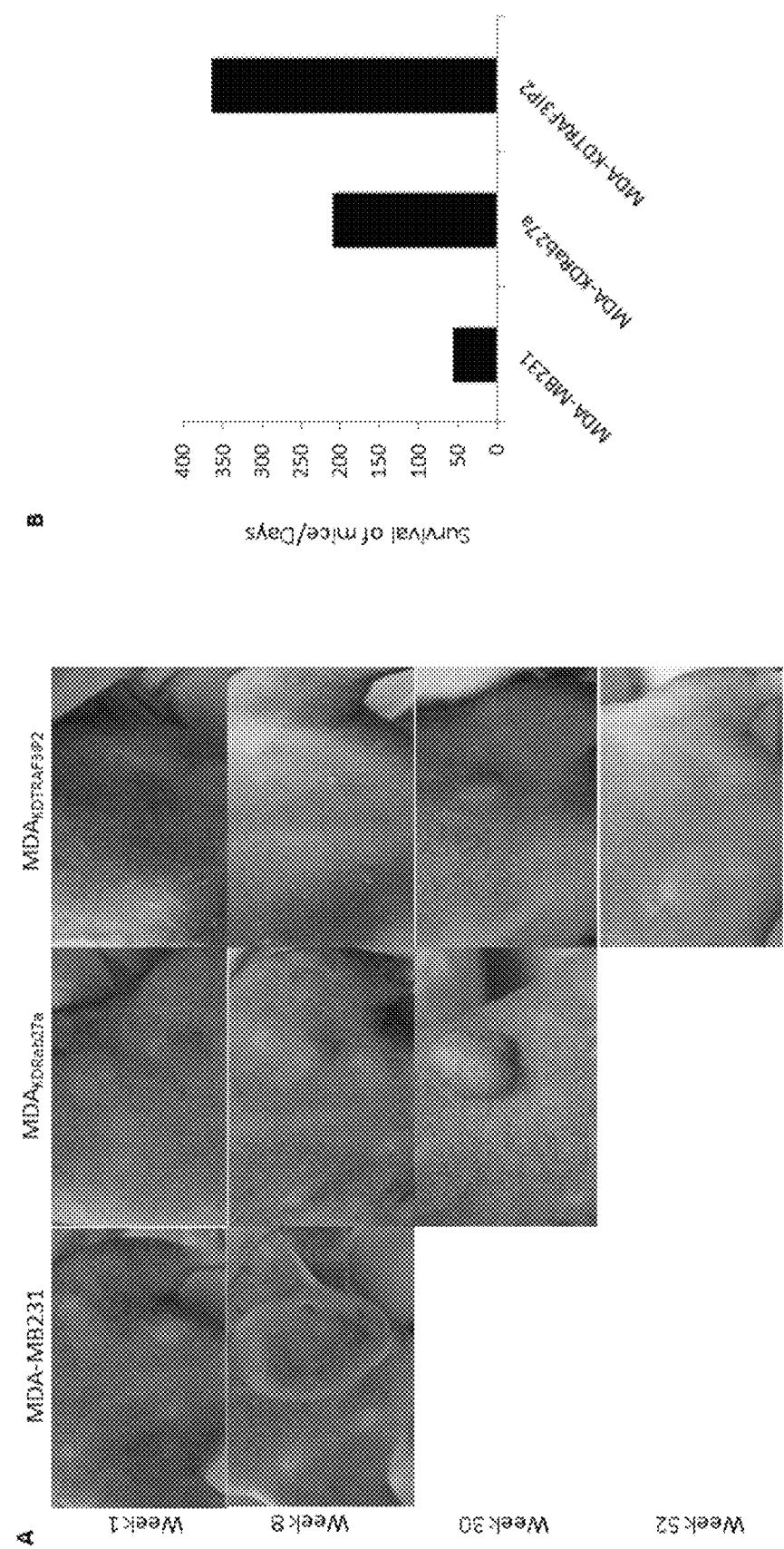
FIG. 6 demonstrates altering tumor microenvironment formation in vivo. A. $1 \times 10^5$ $MDA_{KDTRAF3IP2}$ and $MDA_{KDRAB27A}$ cells in PBS and Martigel were injected intra-mammary in NIHIII female mice (4-6 weeks old). As controls, a group of animals were injected with $1 \times 10^5$ MDA-MB231 cells in PBS and Martigel, another group was injected with Martigel, and another group was injected with PBS (n=15/group). Tumor growth was measured, and control animals injected with MDA-MB231 cells were euthanized 8 weeks post-injection. Animals injected with $MDA_{KDRAB27A}$ cells were euthanized 30 weeks post-injection for further analysis. $MDA_{1TRAF3IP2}$-injected animals showed minimal tumor growth and were euthanized on week 52 of injection for further analysis. B shows a graph illustrating the survival of animals injected with MDA-MB231, MDA$_{KDTRAF3IP2}$ and MDA$_{KDRAB27A}$ cells (P<0.05).

Earlier work showed that breast cancer cells exhibit significantly high levels of RAB27A expression and ultimately have higher exocytosis activity, as shown in FIG. 4A. These in vivo studies showed a decreased tumor volume in $MDA_{KDRAB27A}$ up to 30 weeks post-injection. The control group injected with MDA-MB231 cells showed tumor growth within 8 weeks and the animals were euthanized, as seen in FIG. 6A. Animals injected with $MDA_{KDTRAF3IP2}$ cells survived up to 52 weeks with only limited tumor growth.

Compared to animals injected with MDA-MB231 cells, the survival studies also show a 30 and 52 weeks life span for animals injected with $MDA_{KDRab27}$ and $MDA_{KDTRAF3IP2}$ cells, respectively, as shown by FIG. 6B. These results demonstrate that reducing exocytosis in breast cancer cells attenuates the release of oncogenic molecules into the tumor microenvironment in both soluble and insoluble forms. Silencing TRAF3IP2 regresses tumor growth by reducing cytokine signaling.

Figure 7:
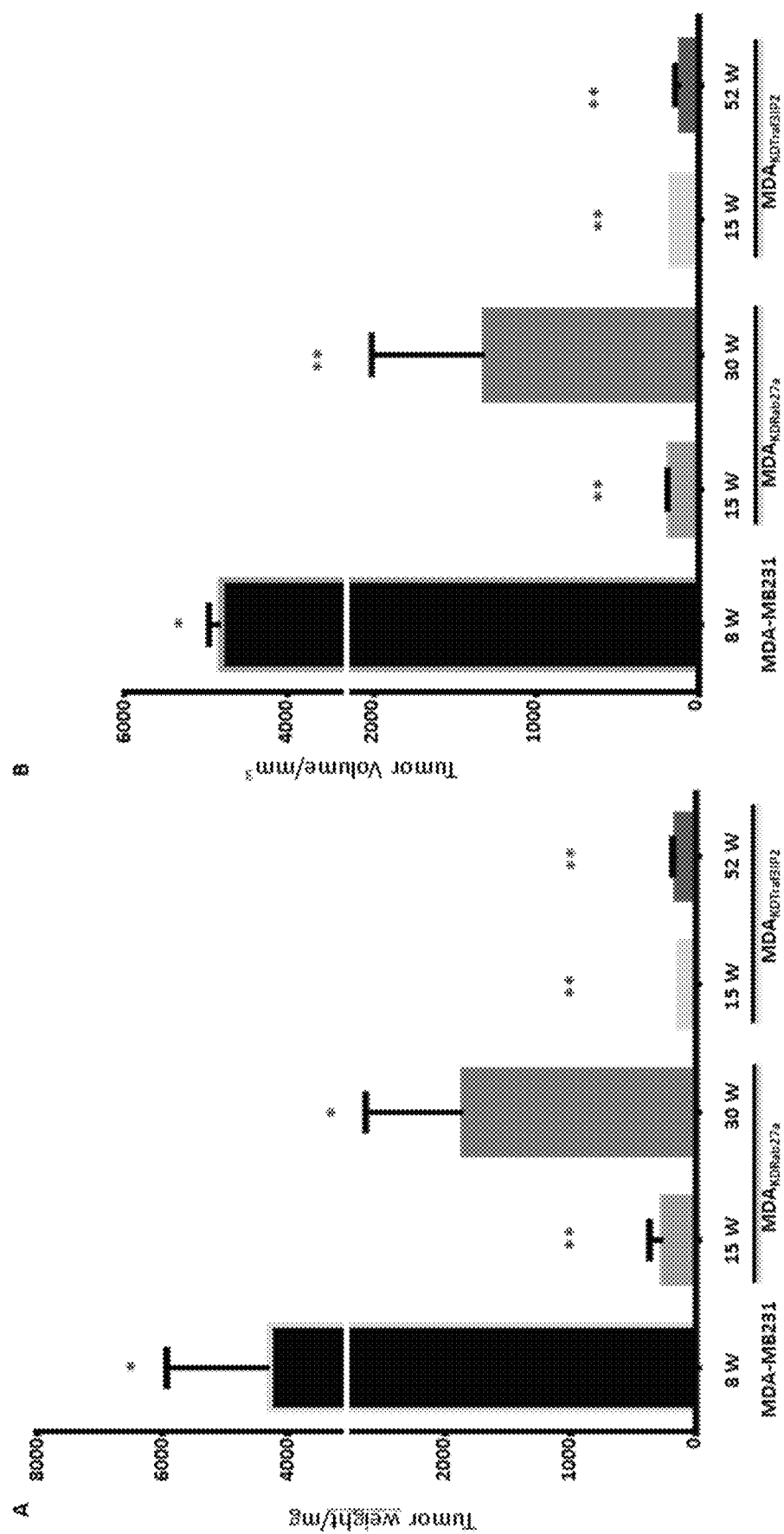
FIG. 7 shows graphs of xenograft tumor weight and volume. Animals injected with MDA-MB231, MDA$_{KDTRAF3IP2}$ and MDA$_{KDRAB27A}$ cells were sacrificed and tumors were isolated and weighted. A illustrates tumor weight and B displays tumor volume in injected animals at different time points.

Upon euthanizing the animals, the tumors were isolated and weighted to quantify the effects of the silencers. FIG. 7A shows the tumor weight and FIG. 7B shows the tumor size at 8 weeks post-injection of MDA-MB231 injected cells, at 30 weeks for $MDA_{KDTRAF3IP2}$ and $MDA_{KDRAB27A}$ cells, and at 52 weeks for $MDA_{KDTRAF3IP2}$ injected cells. These data indicate a significant decrease in tumor growth following down-regulation of TRAF3IP2 and RAB27A.

Thus, the data establishes that silencing TRAF3IP2 and RAB27A in tumor cells prevents tumor growth and/or metastasis in vivo. Injection of MDA-MB231 cells results in metastasis within 8 weeks (data not shown). However, postmortem analysis of animals injected with $MDA_{KDRab27}$ and $MDA_{KDTRAF3IP2}$ showed no metastasis at 30 weeks and 52 weeks post-injection (data not shown).

ΔTRAF3IP2

Delivery of gene silencers is one way of shutting down tRAF3IP2 and/or RAB27a, but knockouts are another possibility and also provide a good biological system in which to study the effects of silencing one or both of these genes.

Using the CRISPR/Cas system, the gene TRAF3IP2 and/or RAD27a can be knocked out. This strategy involves engineering specific nucleases (ex. CAS9-CRISPR) that are designed to create a DNA doublestrand break (DS-break) in the e.g., TRAF3IP2 gene, thereby activating the cell's endogenous homologous recombination repair pathway. Because the DS-break repair mechanisms are not accurate, changes are introduced into the gene by non-homologous end joining (NHEJ), which frequently lead to frame-shift mutations. In this system, CRISPR activation is under strict control of a promoter, such as the IPTG promoter (an analog of lactose). Induction of this promoter activates the TRAF3IP2-specific CRISPR and causes mutations. The delivery of the TRAF3IP2-specific CRISPER lentiviral vectors will be attained by injection to the tumor site. Once the knock-outs are obtained, they can be used in studies to elucidate the biology of this system. Other promoters specific to the respective tumor and under control of tumor-specific, unregulated pathways will also work.

TRAF3IP2 Silencing

The above experiments were performed in an animal model, which mimicked breast cancer tumors. However, those tumors were not localized in the body, but scattered throughout, and especially subcutaneously. On this experiments, we show that the effect is reproducible in wild type mammary fat tumors.

Figure 9:
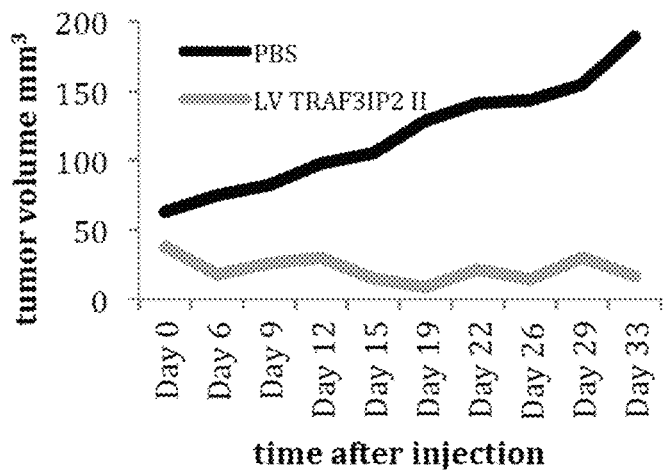
FIG. 9 shows tumor volume in treated animals with lentiviral vector carrying silencing sequence for TRAF3IP2 (Lenti$_{KDTRAF3IP2}$).

Tumors were generated in the mammary fat pad of female immune deficient NIHIII mice. For generating tumors, $5 \times 10^5$ MDA-MB-231 cells were mixed with 50 µl Matrigel and injected into the mammary fat pad. Ten days after injecting the MDA-MB-231 cells, NIH-III mice were randomly divided into two groups. One group of animals was received direct injections of 100 µl lentiviral-vector carrying TRAF3IP2 silencer RNA (in PBS) to the tumor site. The other group (control group), the animals received 100 µl of PBS. Injected tumor volumes were evaluated twice a week by measuring two orthogonal diameters with digital calipers. Tumor volume (V) was calculated using the following equation: $V=(aXb^2)/2$, where "a" is the longer diameter and "b" the shorter diameter FIG. 9. As can be seen, there was little or no tumor growth in those tumors injected with silencer encoding expression vectors. Although the data is not yet available for RAB27A, we predict the results will be similar.

Antisense Oligonucleotide

Oligonucleotides are unmodified or chemically modified single-stranded DNA molecules. In general, they are relatively short (13-25 nucleotides) and hybridize (at least in theory) to a unique sequence in cells. Anti-sense oligonucleotides (ASOs) are single strands of DNA or RNA that are complementary to a chosen sequence. In the case of antisense RNA they prevent protein translation of certain messenger RNA strands by binding to them. If binding takes place, this DNA/RNA hybrid can be degraded by the enzyme RNase H. While the oligonucleotide may be susceptible to rapid degradation by nucleases, a 2'-methoxyethyl (2'-MOE) modified or 2'-O-methyl (2'-OMe) modified ASO is resistant to nucleases and has enhanced target binding and pharmacokinetics comparing to DNA. Therefore, the ASOs employed herein can be 2'-MOE or 2'-OMe modified or unmodified.

The inventors therefore investigated the possibility of silencing TRAF3IP2 with oligonucleotides and especially with more degradation-resistant oligonucleotides, as well as the suitable target binding sites within the gene.

Figure 17A:
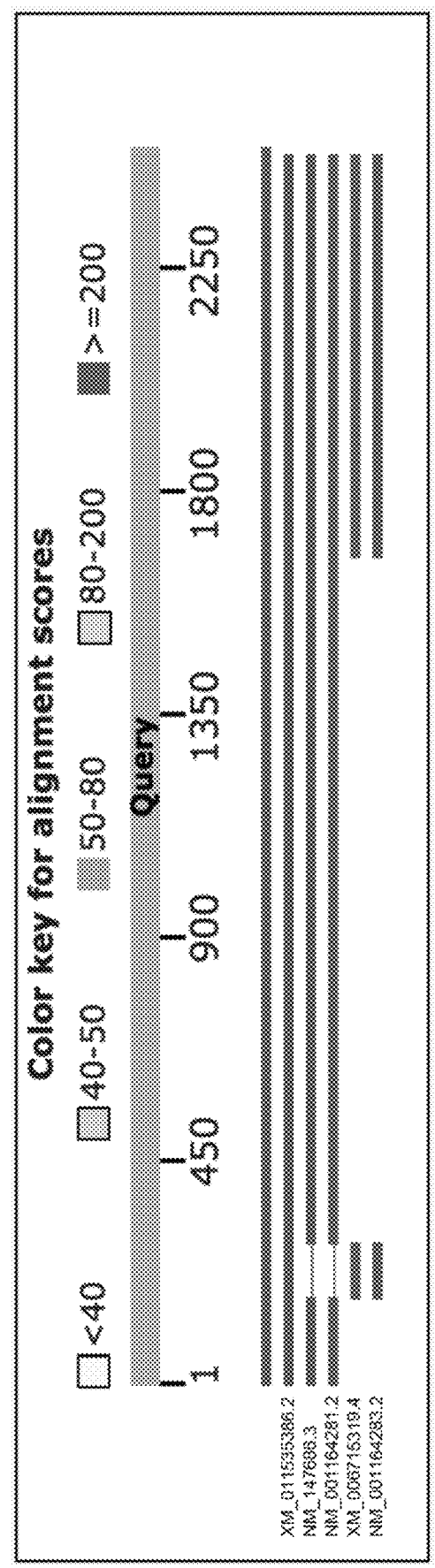
FIG. 17A. TRAF3IP2 mRNA variants comparison.

Several variants of NM_147200.2 (SEQ ID NO. 8) were investigated, including XM_011535386.2 (SEQ ID NO. 9), NM_147686.3 (SEQ ID NO. 10), NM_001164281.2 (SEQ ID NO. 7), XM006715319.4 (SEQ ID NO. 11), and NM_001164283.2 (SEQ ID NO. 12). Highly conserved regions appear in these sequences, as shown in FIG. 17A, suggesting that target binding sequence may be available within the conserved regions. TRAF3IP2 gene has 10 exons, among which exons 9 and 10 are conserved across the known variants. By targeting the most conserved regions across all variants, these oligonucleotides are believed to be able to block most of the TRAF3IP2 activity. Therefore, anti-sense oligonucleotides (ASOs) can be designed to specifically target these exons to obtain more universal applicability.

TRAF3IP2 Silencing in Glioblastoma

The above experiments were performed using breast cancer cell lines, but we also hoped that the method might be applicable to other solid tumors, and thus tested a glioblastoma derived cell line to confirm.

TRAF3IP2 exhibit significant role in the onset of tumor microenvironment and metastasis in solid tumors including Glioblastoma. TRAF3IP2, a signaling adaptor involved in the regulation of adaptive immunity operates as a positive signaling adaptor in IL-17-mediated cellular immune responses. IL-17 is a dominant 'signature' cytokine of TH-17 cells and up regulates neutrophil-mobilizing cytokines, chemokines, and tissue-degrading matrix metalloproteases17. IL-17-dependent receptor ligation induces TRAF3IP2 recruitment to the cytoplasmic tail of the IL-17R. This in turn allows the incorporation of the TNF receptor associated factors (TRAF) TRAF3 and TRAF6 into the signaling complex and the subsequent downstream activation of the MAPK and NF-κB pathway. Accordingly, TRAF3IP2 is not only involved in pathways balancing humoral and cellular immunity, but it also represents a chief link between IL-17 mediated adaptive immune responses and NF-κB as the master regulator of innate immunity controlling the inducible transcription of various pro-inflammatory cytokines.

Previously, our group and others showed that TRAF3IP2 mediates IKK dependent NF-kB activation as well as TLR4 signaling. It has been shown that IL-17 signals exclusively via TRAF3IP2, and TRAF3IP2 gene deletion abrogates IL-17-dependent inflammatory signaling.

We have shown a significantly high expression of TRAF3IP2 in breast cancer cells while this expression is minimal in non-malignant breast epithelial cells and MSCs. Our data indicate that similar to breast cancer, significant amounts of TRAF3IP2 express in glioblastoma cells (data not shown). Herein, we have studied the effect of TRAF3IP2 silencing on in vitro and in vivo characteristics of a glioblastoma cell line (U87).

Figure 10:
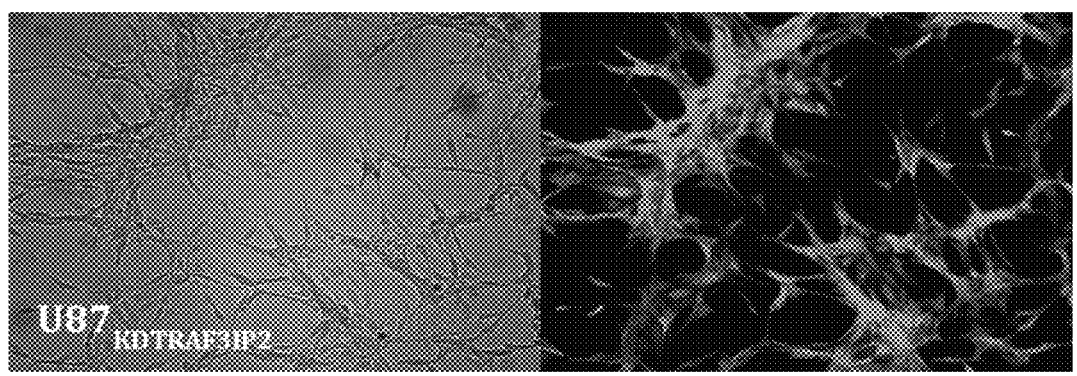
FIG. 10 is a photograph of U87 cells (a glioblastoma cell line) transduced with lentiviral vector carrying a silencing sequence for TRAF3IP and GFP (green).
Figure 11:
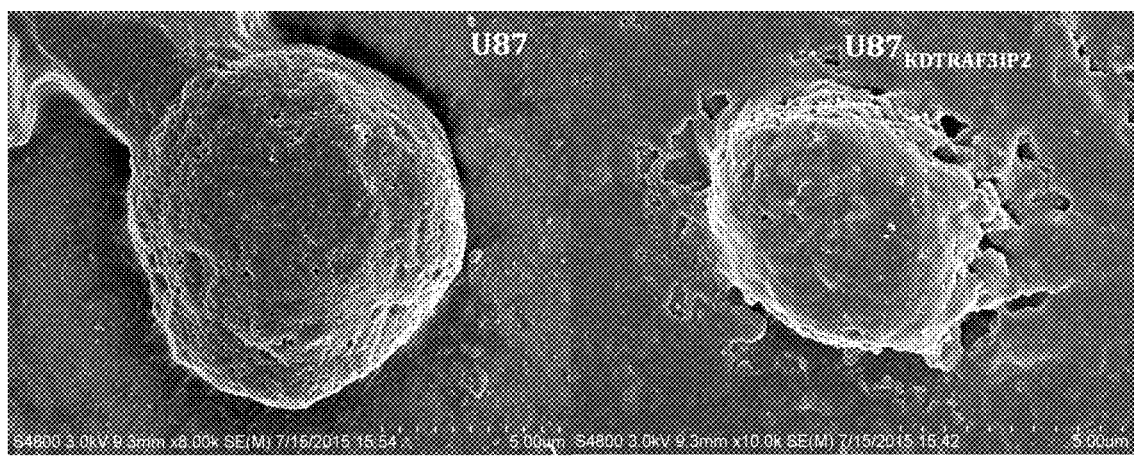
FIG. 11 shows a scanning electron micrograph showing morphological changes in U87$_{KDTRAF3IP2}$ compared to wild type U87.
Figure 12:
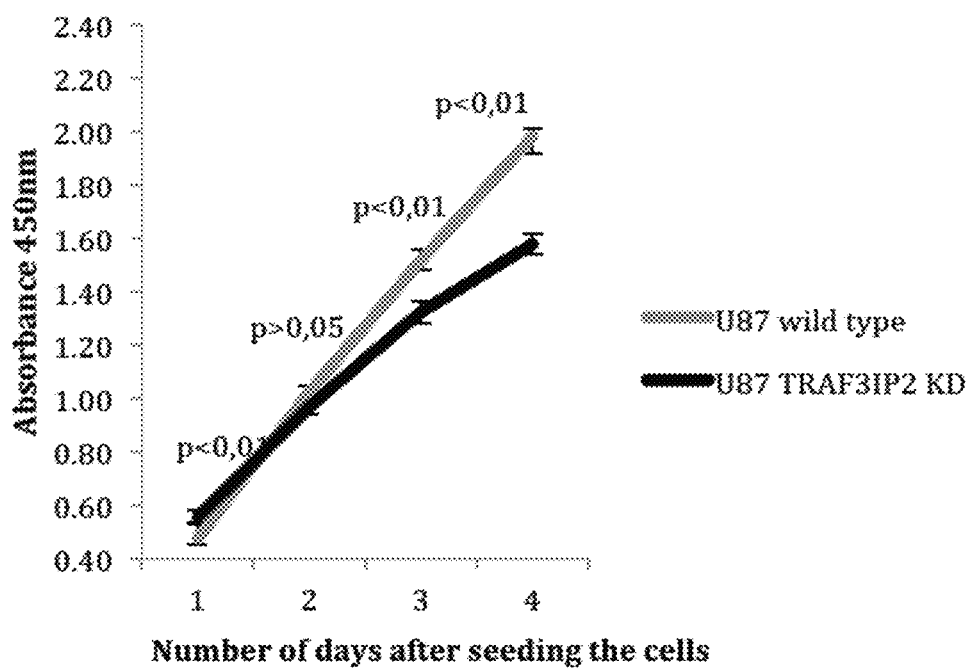
FIG. 12 is a cell proliferation assay showing a slight decrease in U87$_{KDTRAF3IP2}$ cell proliferation, as compared to the U87 wild type cell.

A human glioblastoma cell line "U87 cells" were transduced with lentiviral vector carrying a silencing sequence for TRAF3IP2 and GFP as a detectable marker. As can be seen in FIG. 10 transduced U87 cells with lentiviral delivering silencer sequences for TRAF3IP2. A GFP expressing sequence was used as a reporter gene making transduced cells traceable. In addition, electron microscopic analysis showed morphological changes in U87KDTRAF3IP2 compared to wild type U87 (FIG. 11). These changes include a different cell morphology, which might be related to modified cellular function due to silencing TRAF3IP2.

Figure 13:
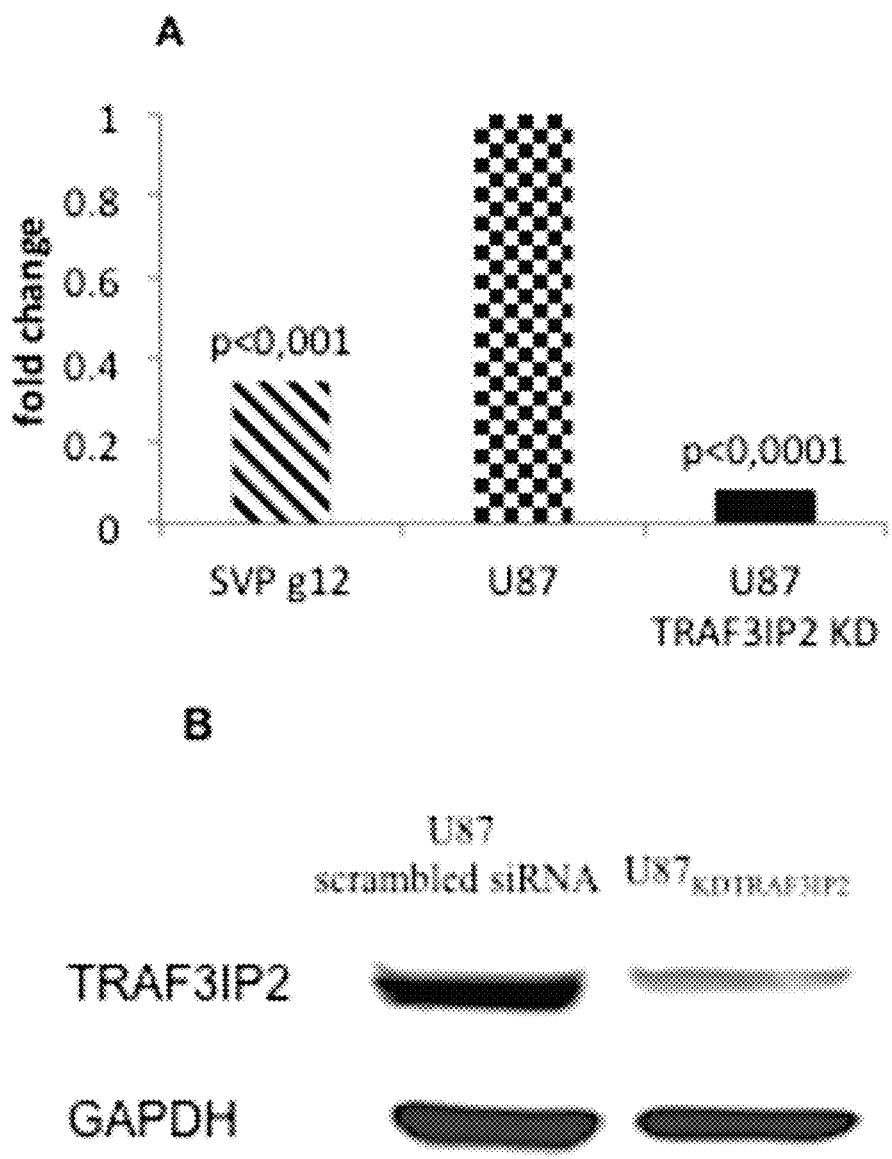
FIG. 13 shows TRAF3IP2 gene (A) and Protein (B) expression levels. Wild type U87 were transduced with is scrambled silencer RNA (SVg12) and used as control in these experiments. Scrambled shRNA is a non-target silencer RNA, which is used as a control in these experiments.

A cell proliferation assay shown in FIG. 13 shows only a slight decrease in $U87_{KDTRAF3IP2}$ cell proliferation, as compared with the control cell U87, which suggests that the effect of the silencer is not a direct effect on cell proliferation, but an indirect one on the interaction of the tumor cells with its microenvironment.

Figure 14:
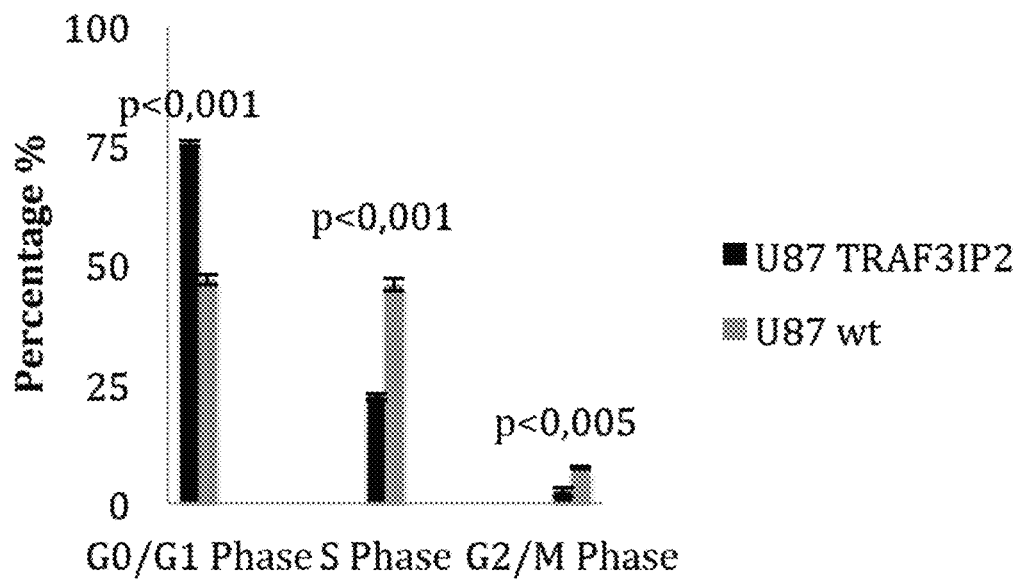
FIG. 14 is a cell cycle analysis of U87$_{KDTRAF3IP2}$ and wild type U87.

When we studied gene and protein expression levels, TRAF3IP2 expression was significantly reduced in both gene and protein levels in $U87_{KDTRAF3IP2}$ compared to control U87 and U87 transduced with scrambled silencer RNA (up to 92.3%), confirming that the silencer was effective in these cells. The results are shown in FIGS. 14A and 14B which provides the TRAF3IP2 gene and protein expression, respectively.

Figure 15:
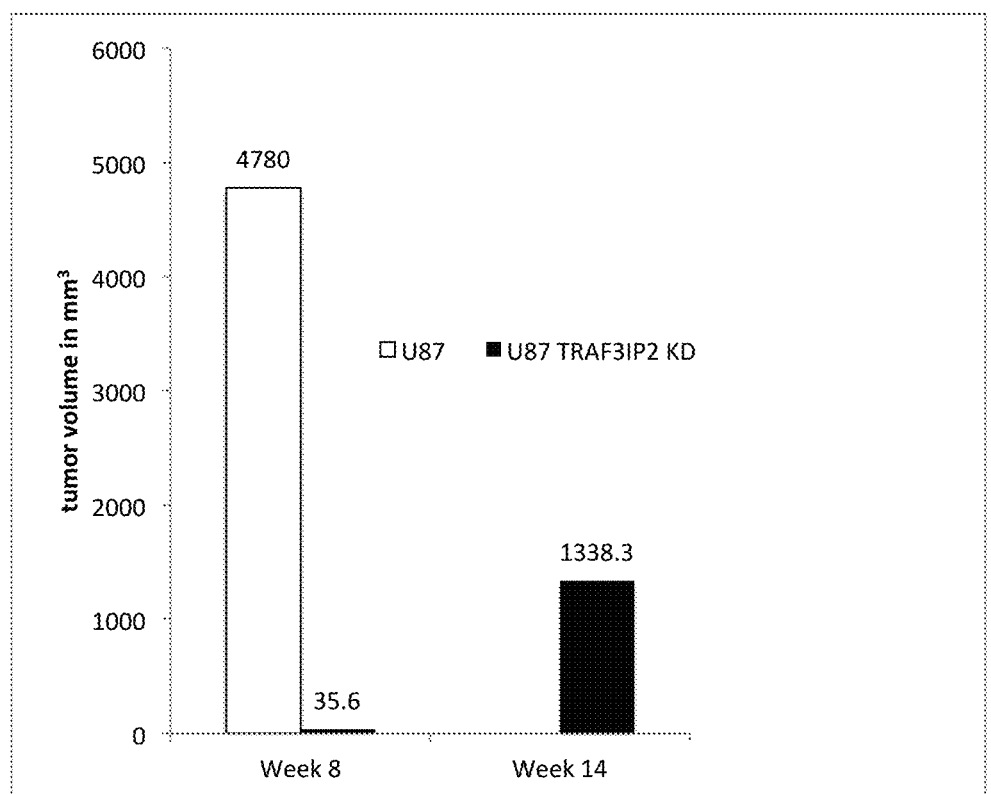
FIG. 15 shows the in vivo tumorigenesis of U87$_{KDTRAF3IP2}$ cells. Tumor size was measured using caliper and volume calculated and plotted here against time.

Cell cycle analysis also showed significant changes in cell cycle profile in $U87_{KDTRAF3IP2}$ compared to wild type U87. As seen in FIG. 15, silencing TRAF3IP2 caused higher G1 phase and lower populations in S and G2 phases, which might indicate a lower U87 replication rate.

To further test the theory and broaden the possible silencing alternatives, highly effective anti-sense oligonucleotides (ASOs) were designed to target TRAF3IP2. Six (6) exemplary ASOs were designed (SEQ ID NOs. 13-18), for example, ASO1 and ASO2 are shown in FIG. 17B. It is to be noted that the length of the AOs can vary while achieving similar silencing effect.

Figure 18:
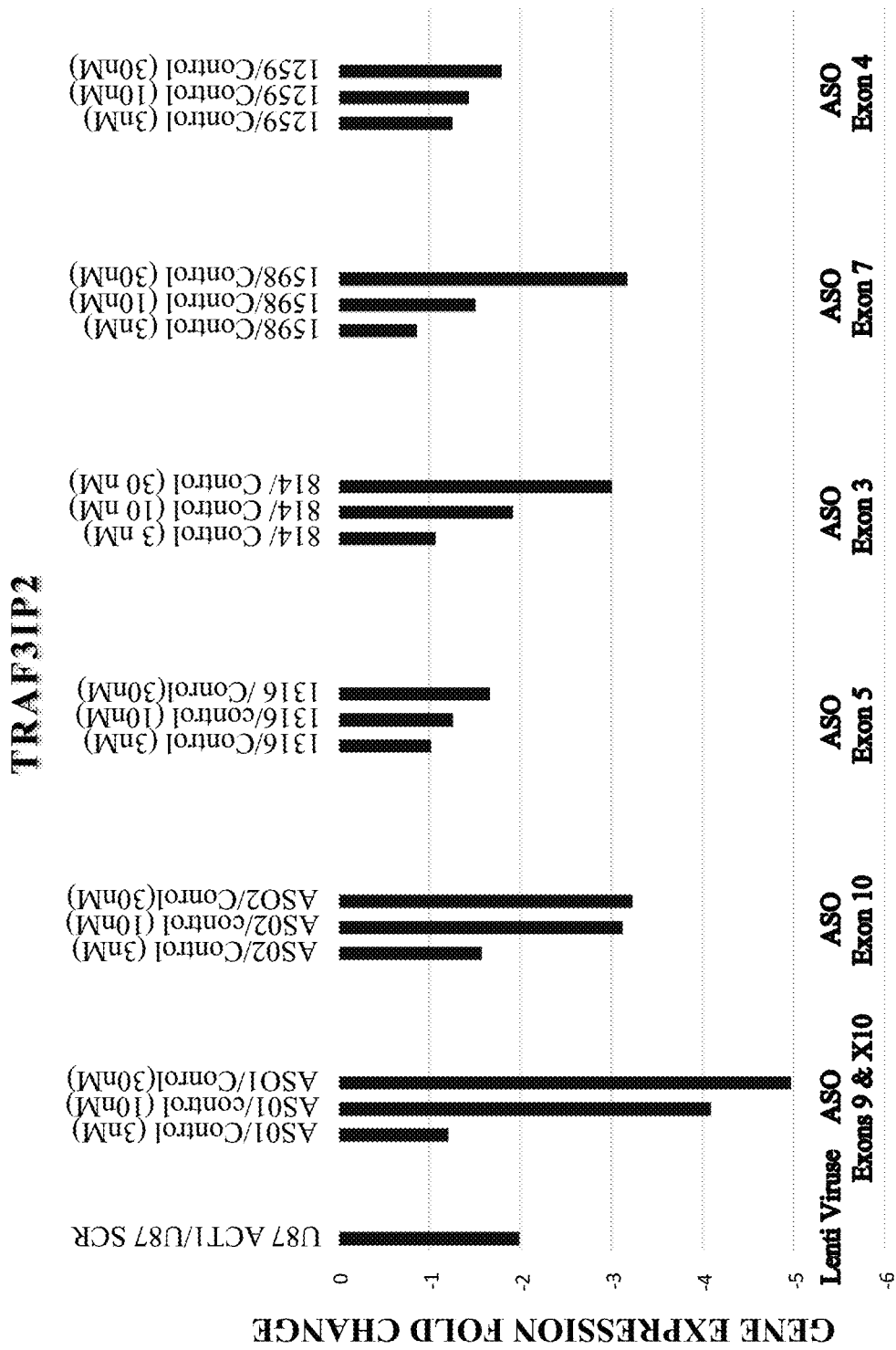
FIG. 18. Selection and optimization of ASOs in targeting TRAF3IP2 in glioblastoma cells.

The six AOs were tested for their ability to silence the expression of TRAF3IP2 in glioblastoma cells (FIG. 18) using the lentiviral vector. As shown in FIG. 18, concentration-dependent silencing effects were demonstrated by all six ASOs. Among the six, ASO1, ASO2, ASO4, and ASO5 showed comparable or better silencing capability comparing to the control. The ASO1 significantly suppresses TRAF3IP2 in glioblastoma cells, comparing to other possible ASOs.

Experiments can also be designed to test the silencing effect of the ASOs across different cell lines from different tissues, in order to validate their efficacy on the TRAF3IP2 variants. It is expected that similar silencing of TRAF3IP2 expression can be achieved because these ASOs are designed to target only the conserved regions across known variants.

It is also contemplated that personalized silencing can be achieved, as the cost of producing the silencing sequences will continue to decline. As such, the need to target only the conserved regions across TRAF3IP2 variants may be obviated. Certain regions within TRAF3IP2 may be even more susceptible to silencing on an individualized basis, and the inventive concept described herein can be readily applied.

In Vivo Tumorigenicity of U87KDTRAF3IP2

The above experiments strongly suggested that TRAF3IP2 silencer might also be effective in gliobalstoma tumors, but the results needed to be confirmed in an in vivo system. Therefore, we created U87 glioblastoma-like tumors by injecting these cells into nude mice.

U87$_{KDTRAF3IP2}$ and wild type U87 cells were injected subcutaneously in the upper portion of the right hind thigh. Tumors were measured with a traceable digital caliper (Fisher Scientific) for calculation of the tumor volume. The tumor size and volume were measured weekly. The animals injected with U87$_{KDTRAF3IP2}$ showed a significantly smaller tumor size compared to control animals injected with wild type U87. The control animals were sacrificed 8 weeks following injection. The animals injected with U87$_{KDTRAF3IP2}$ which were sacrificed on week 14 post-injection, showed significantly smaller tumor volume. This confirms that TRAF3IP2 silencing can also slow gliobablastoma tumor growth in vivo.

Treatment of U87 tumors are also under investigation. The efficacy of ASOs will be tested by following a protocol for obtaining and implanting tumors, and for data collection. However, targeting modality will be injections of ASO. After confirming tumors 14 days after initial implantation, animals will be treated with TRAF3IP2-ASO, which we have designed and optimized for targeting efficacy and efficiency) through ICV injections in the lateral ventricle (5 µl every 48 h for 40 days; 30 nM concentration). The animals will be followed for up to 32 weeks post-tumor induction. Scrambled-ASO will serve as a control. Preliminary data shows a significant decrease in tumor development and growth on treated animals with lentiviral carrying silencer RNA injected to tumor site.

Figure 19:
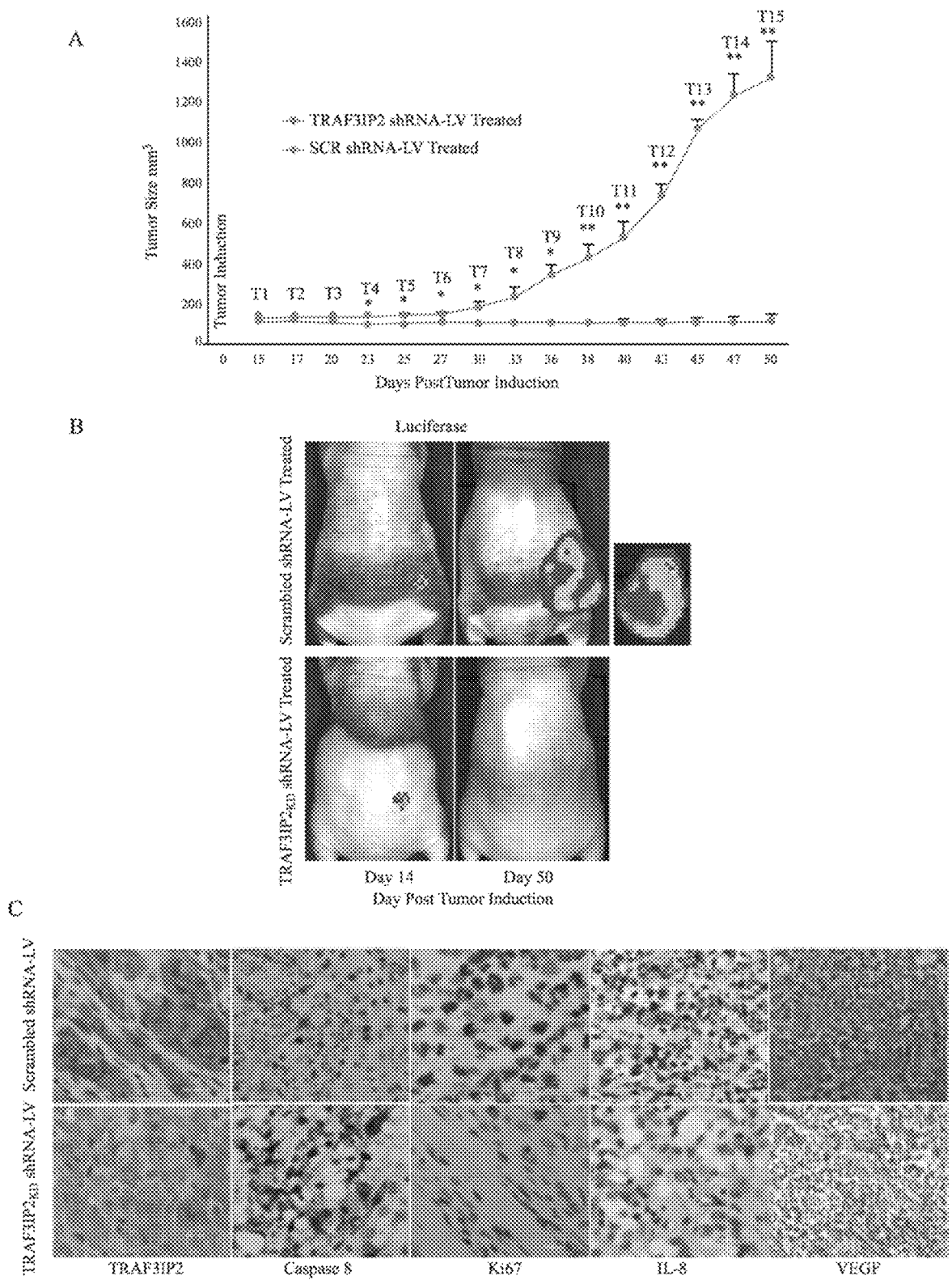
FIG. 19. Effect of silencing TRAF3IP2 in a flank xenograft model. A. Suppression of glioblastoma tumors by TRAF3IP2 shRNA-LV injected subcutaneously onto tumors compared to scrambled shRNA-LV injected tumors. Frequency of administration is shown in the graph. B. Tumor size was measured biweekly ($^+$P<0.05; $^{++}$P<0.001). C. Animals imaged for luciferase weekly. Immunohistochemical localization of TRAF3IP2, caspase 8, Ki67, IL-8, and VEGF in tumors treated with TRAF3IP2 shRNA-LV or scrambled shRNA-LV. Scale: 100 μm.

Therapeutic Significance of Targeting TRAF3IP2 in the Regression of Pre-Existing Glioblastoma Tumors Having demonstrated that TRAF3IP2-silenced malignant U87 glioblastoma cells form significantly smaller tumors, we next determined whether treating existing tumors by lentiviral TRAF3IP2 shRNA regresses their size. In this translationally important strategy, tumors were induced at first by injecting luciferase-labeled U87 cells into the flank region of immunodeficient NIH-III mice. Fourteen days later, when tumors were distinctively quantifiable, lentivirus expressing GFP-tagged TRAF3IP2 shRNA (TRAF3IP2 shRNA-LV) was injected subcutaneously onto the tumors. Scrambled shRNA-LV served as a control. Results in FIG. 19A show a remarkable reduction in tumor size over 50 days post-induction in TRAF3IP2 shRNA-LV-treated animals (versus scrambled shRNA-LV; 0.08±0.03 g versus 1380±48, respectively) (FIG. 19B). Analysis of residual tumors by IHC revealed a marked reduction in TRAF3IP2, Ki67, IL-8 and VEGF expression (FIG. 19C), but a significant increase in caspase 8 levels (FIG. 19C).

The results show that treating existing tumors formed by the wild type U87 glioblastoma cells with TRAF3IP2 shRNA significantly reduces tumor size in the flank xenograft model.

TRAF3IP2 Silencing in Glioblastoma Angiogenesis

It is also reported that TRAF3IP2 contributes to angiogenesis, an important aspect of tumor growth and metastasis. Inhibiting angiogenesis has been widely reported to show hope in tumor treatment. Therefore, silencing TRAF3IP2 could play a major role in controlling or reducing tumor size and reduce metastasis.

Our results indicate that silencing TRAF3IP2 leads to reduced expression of VEGFA (12-fold reduction), a key growth factor in angiogenesis. Additional in vitro experiments also showed that TRAF3IP2 silencing significantly reduced angiogenesis in U87 cells. It is therefore proposed that silencing TRAF3IP2 could be used to treat tumors expressing high level of TRAF3IP2, as well as preventing its metastasis.

Future experiments include studies to confirm silencer delivery to mammary tumors, with preferred delivery agents such as MSCs. Of course, clinical studies will be performed eventually to confirm efficacy of these methods in humans, but these experiments are expected to take several years.

The following reference are incorporated by reference herein in its entirety for all purposes:

Gehmert, S. et al. (2010). "Breast cancer cells attract the migration of adipose tissue-derived stem cells via the PDGF-BB/PDGFR-b signaling pathway." Biochemical and Biophysical Research Communications 398, 601-605.

Hunter, C. A. (2007). "Activating IL-17 inflammation." Nat Immunol 8(3): 232-4.

Ilmer, M. et al. (2014). "Two sides of the same coin: stem cells in cancer and regenerative medicine." FASEB J. 28(7):2748-61.

Muehlberg, F. L. et al. (2009). "Tissue-resident stem cells promote breast cancer growth and metastasis." Carcinogenesis 30(4) 589-97.

Qian, Y., C. Liu, et al. (2007). "The adaptor Act1 is required for interleukin 17-dependent signaling associated with autoimmune and inflammatory disease." Nat Immunol 8(3): 247-56.

Senst, C., T. Nazari-Shafti, et al. (2013). "Prospective dual role of mesenchymal stem cells in breast tumor microenvironment." Breast Cancer Res Treat 137(1): 69-79.

WO2014030602 An agent for treating cancer

Xia Y F, et al., Identification of alternatively spliced Act1 and implications for its roles in oncogenesis, Biochem. Biophys. Res. Commun. 296 (2): 406-12 (2002).

What is claimed is:

1. A pharmaceutical composition for the treatment of a tumor having increased expression of TRAF3IP2, wherein said composition comprises at least one silencing sequence for TRAF3IP2 in a pharmaceutically acceptable carrier in an amount effective for the therapeutic treatment of a tumor, wherein said silencing sequence reduces the expression of the TRAF3IP2 gene by at least two-fold as comparing to without the silencing sequence for TRAF3IP2, and wherein said silencing sequence is a modified portion of sense strand of NM_001164281.2 (SEQ ID NO. 7), NM_147200.2 (SEQ ID NO. 8), XM_011535386.2 (SEQ ID NO. 9), NM_147686.3 (SEQ ID NO. 10), XM006715319.4 (SEQ ID NO. 11), and NM_001164283.2. (SEQ ID NO. 12) corresponding to exon 9 and/or exon 10 of TRAF3IP2.

2. The composition of claim 1, wherein said composition comprises an expression vector encoding a TRAF3IP2 silencer operably coupled to an inducible promoter.

3. The composition of claim 1, wherein said silencing sequence is an siRNA, an miRNA, an shRNA, an antisense RNA, or an antisense oligonucleotide.

4. The composition of any of claim 1, said silencing sequence encoded by an expression vector hosted in a mesenchymal stem cell (MSC) that targets said tumor.

5. The composition of claim 4, said MSC having been previously exposed to exosomes from said tumor.

6. The composition of claim 3, wherein said silencing sequence is an antisense oligonucleotide that is 13-25 nucleotides in length.

7. The composition of claim 6, wherein the antisense oligonucleotide is complementary to a portion of the sense strand of any one of SEQ ID NOs. 7-12.

8. The composition of claim 6, wherein the antisense oligonucleotide is selected from SEQ ID NOs. 13-18.

9. The composition of claim 1, wherein the pharmaceutically acceptable carrier is a nucleic acid carrier.

10. The composition of claim 1, further comprising a silencing sequence for Rab27a.

11. The composition of claim 1, wherein said composition is formulated for parenteral administration, including direct injection into a tumor or its metastasis site by transcutaneous, intraarterial, intraductal, intravenous, intradermal, intramuscular, intraperitoneal, or subcutaneous administration.

12. The composition of claim 1, wherein the composition is used in treating glioblastoma or breast cancer, or for use in treating any cancer with at least 2-fold increased TRAF3IP2 and/or Rab27a expression.

13. A method of treating at least one tumor in a mammal comprising administering to the mammal an effective amount of the composition of claim 1.

14. The method of claim 13, wherein said tumor is a solid tumor or breast cancer or a glioblastoma or a cancer with at least 2 fold increased expression of TRAF3IP2 or Rab27a or both.

15. The method of claim 13, wherein the composition is injected directly into said tumor and said injection is guided by ultrasound, fluoroscopy, imaging, CT, MRI, or visually, in order to enhance the local concentration of the silencer within the tumor.

16. A method to selectively treat a tumor and minimize side effects, by administering an effective amount of a silencer for TRAF3IP2 to a tumor that expresses at least 10 times the amount of TRAF3IP2, as compared to a non-tumor cell from the surrounding tissue, wherein the silencer for TRAF3IP2 comprises the silencing sequence of claim 1.

17. The method of claim 16, wherein said silencer is an siRNA, an miRNA, an shRNA, an antisense RNA, or an antisense oligonucleotide.

18. The method of claim 16, further comprising enhancing the selective effect on tumor cells and avoiding effects on non-tumor cells by increasing the local concentration of the silencer within the tumor by injecting said silencer(s) directly into said tumor.

19. The method of claim 16, wherein said silencer(s) is encoded in an expression vector having an inducible promoter, thus enhancing the selective effect on tumor cells and avoiding effects on normal cells by selectively activating the production of the silencer by a switch that activates said inducible promoter.

20. The method of claim 16, wherein said silencer(s) is linked to an antibody, or other targeting substance specific to said tumor.

21. A silencing sequence of TRAF3IP2 for use as a medicament or for use in treating a tumor, or solid tumor, or for use in treating glioblastoma or breast cancer, or for use in treating any cancer with at least 2-fold increased TRAF3IP2 expression, wherein said silencing sequence is a modified portion of sense strand of NM_001164281.2 (SEQ ID NO. 7), NM_147200.2 (SEQ ID NO. 8), XM_011535386.2 (SEQ ID NO. 9), NM_147686.3 (SEQ ID NO. 10), XM006715319.4 (SEQ ID NO. 11), and NM_001164283.2. (SEQ ID NO. 12).

* * * * *

SEQUENCE LISTING

<160> NUMBER OF SEQ ID NOS: 18

<210> SEQ ID NO 1
<211> LENGTH: 58
<212> TYPE: DNA
<213> ORGANISM: Homo sapiens

<400> SEQUENCE: 1
ccggcatgga actatcatta ccattctcga gaatggtaat gatagttcca tgtttttt          58

<210> SEQ ID NO 2
<211> LENGTH: 59
<212> TYPE: DNA
<213> ORGANISM: Homo sapiens

<400> SEQUENCE: 2
ccggccgtga tgataatcgt agcaactcga gttgctacga ttatcatcac ggttttttg         59

<210> SEQ ID NO 3
<211> LENGTH: 59
<212> TYPE: DNA
<213> ORGANISM: Homo sapiens

<400> SEQUENCE: 3
ccgggcttca gaacactcat gtctactcga gtagacatga gtgttctgaa gcttttttg         59

<210> SEQ ID NO 4
<211> LENGTH: 57
<212> TYPE: DNA
<213> ORGANISM: Homo sapiens

<400> SEQUENCE: 4
ccggcggatc agttaagtga agaaactcga gtttcttcac ttaactgatc cgttttt          57

<210> SEQ ID NO 5
<211> LENGTH: 57
<212> TYPE: DNA
<213> ORGANISM: Homo sapiens

<400> SEQUENCE: 5
ccgggctgcc aatgggacaa acatactcga gtatgtttgt cccattggca gctttttt        57

<210> SEQ ID NO 6
<211> LENGTH: 57
<212> TYPE: DNA
<213> ORGANISM: Homo sapiens

<400> SEQUENCE: 6
ccgggctgcc aatgggacaa acatactcga gtatgtttgt cccattggca gctttttt        57

<210> SEQ ID NO 7
<211> LENGTH: 6241
<212> TYPE: DNA
<213> ORGANISM: Homo sapiens

<400> SEQUENCE: 7
aatgctgatg tttttaagcag ttagaggagg tggaagaagc tcgactccct cttcttcccc      60
attatctgcc cacaatcccc tcctttggag ctgctaatga ttactaattc ttaacattcg      120
agttcaatct cctcccggag acaccctccc aggcgagggc actgcgacta cactgaggtt      180
ctgcccactc ctgggcagct tcttagctgg gtggcgaaaa caaaaatgcc gcctaattgg      240
tcactggccc tttctcatga atgaaggagg tttctgtttt aagaaataaa gtgactcctc      300

-continued

```
agccgttgat tcactgccca cagggagatt ttgagcagag gcttcctagg ctccgtagaa    360
atttgcatac agcttccact tcctgcttca gagcctgttc ttctacttac ctgggcccgg    420
agaaggtgga gggagacgag aagccgccga gagccgacta ccctccgggc ccagtctgtc    480
tgtccgtggt ggatctaaga aactagaatg aaccgaagca ttcctgtgga ggttgatgaa    540
tcagaaccat acccaagtca gttgctgaaa ccaatcccag aatattcccc ggaagaggaa    600
tcagaaccac ctgctccaaa tataaggaac atggcaccca acagcttgtc tgcacccaca    660
atgcttcaca attcctccgg agacttttct caagctcact caaccctgaa acttgcaaat    720
caccagcggc ctgtatcccg gcaggtcacc tgcctgcgca ctcaagttct ggaggacagt    780
gaagacagtt tctgcaggag acacccaggc ctgggcaaag cttccccttc tgggtgctct    840
gcagtcagcg agcctgcgtc tgagtctgtg gttggagccc tccctgcaga gcatcagttt    900
tcatttatgg aaaaacgtaa tcaatggctg gtatctcagc tttcagcggc ttctcctgac    960
actggccatg actcagacaa atcagaccaa agtttaccta atgcctcagc agactccttg   1020
ggcggtagcc aggagatggt gcaacggccc cagcctcaca ggaaccgagc aggcctggat   1080
ctgccaacca tagacacggg atatgattcc cagccccagg atgtcctggg catcaggcag   1140
ctggaaaggc ccctgcccct cacctccgtg tgttaccccc aggacctccc cagacctctc   1200
aggtccaggg agttccctca gtttgaacct cagaggtatc cagcatgtgc acagatgctg   1260
cctcccaatc tttccccaca tgctccatgg aactatcatt accattgtcc tggaagtccc   1320
gatcaccagg tgccatatgg ccatgactac cctcgagcag cctaccagca agtgatccag   1380
ccggctctgc ctgggcagcc cctgcctgga gccagtgtga gaggcctgca ccctgtgcag   1440
aaggttatcc tgaattatcc cagccccctgg gaccacgaag agaggcccgc acagagagac   1500
tgctcctttc cggggcttcc aaggcaccag gaccagccac atcaccagcc acctaataga   1560
gctggtgctc ctggggagtc cttggagtgc cctgcagagc tgagaccaca ggttccccag   1620
cctccgtccc cagctgctgt gcctagaccc cctagcaacc ctccagccag aggaactcta   1680
aaaacaagca atttgccaga gaattgcgg aaagtctta tcacttattc gatggacaca   1740
gctatggagg tggtgaaatt cgtgaacttt ttgttggtaa atggcttcca aactgcaatt   1800
gacatatttg aggatagaat ccgaggcatt gatatcatta aatggatgga gcgctacctt   1860
agggataccg tgatgataat cgtagcaatc agccccaaat acaaacagga cgtggaaggc   1920
gctgagtcgc agctggacga ggatgagcat ggcttacata ctaagtacat tcatcgaatg   1980
atgcagattg agttcataaa acaaggaagc atgaatttca gattcatccc tgtgctcttc   2040
ccaaatgcta agaaggagca tgtgcccacc tggcttcaga acactcatgt ctacagctgg   2100
cccaagaata aaaaaaacat cctgctgcgg ctgctgagag aggaagagta tgtggctcct   2160
ccacgggggc ctctgcccac ccttcaggtg gttcccttgt gacaccgttc atccccagat   2220
cactgaggcc aggccatgtt tggggccttg ttctgacagc attctggctg aggctggtcg   2280
gtagcactcc tggctggttt ttttctgttc ctccccgaga ggccctctgg cccccaggaa   2340
acctgttgtg cagagctctt ccccggagac ctccacacac cctggctttg aagtggagtc   2400
tgtgactgct ctgcattctc tgcttttaaa aaaccattg caggtgccag tgtcccatat   2460
gttcctcctg acagtttgat gtgtccattc tgggcctctc agtgcttagc aagtagataa   2520
tgtaagggat gtggcagcaa atggaaatga ctacaaacac tctcctatca atcacttcag   2580
gctactttta tgagttagcc agatgcttgt gtatcctcag accaaactga ttcatgtaca   2640
```

```
aataataaaa tgtttactct tttgtaagat tatgtttttac ttatctcaaa ggagatacat    2700
ataatttata atgatatggg cagttgcttc cagggacatc aacaaagctg cttagatata    2760
atattagata aatataacag accactctgt attaatggat taaagccagc tagttaaaca    2820
acccttttta accataatca tggaagcttt attcttgcaa taaagatttt taggctgggc    2880
gcagtgactc acacctgtaa tcccagcact tgggaagct aaggcaggca gatcatttga     2940
ggtcaggagt ttgagaccag cctggccaac atggtgaaac cccatctctg ctaaaattac    3000
aaaaaagtta gccgggcatg gtggtgtgca cctgtaatcc cagctactcg ggaggctgag    3060
gcaggagaat cacttgaacc cgggaggcag aggttgcagt gagccgagat catgtcactg    3120
cactctagct tgggagacag agcgagactc cgtctcaaaa aacaaacaaa caaataaaaa    3180
cacccatttt taacaaaaca actttatata gcatacagcc atgattctaa atagtatgat    3240
tatggttctc aggatctgac tacataggta aaaatatttg catatgtgta tgaagtgttg    3300
ggggatgtag gctagaattg tagtctgtgt tctaattttg gttctaccac caattagctg    3360 tatgacctttt agcaagtcct ttaacttttc ttagattcca gggactcatt tataaaatga    3420 catgacaaa agcatctcta atcactctaa aagatttgaa gtctaggacc taaattctaa     3480
atactctttt gaggagtgac tgagttttca ttttcataat tatgtctctc agaggacaaa    3540
tttacatttt cttaacagag acattttctt cttctttttt tttgtttgag acagagtctc    3600
gctctgtcgt ccaggctgga gtgcagtgct gcaatcttgg ctcactgcaa cctgcgcctc    3660
ctgggttcaa gtgattcttc tgcctcaacc tcccaagtag ctagacctat aggcgcctgc    3720
caccatgccc agctaatttt tgtatttta gtagagacag gtttcatat tggccagact      3780 ggtctcgaac tcctgacctt gtgatccgcc cacctcggcc tcccaaagtg ctgggattac    3840
aggtgtgagc caccacaccc agccaacatt ttcctctttt aaaaaatatc ttctcacgcc    3900
tgtaatccca gcactttggg aggctgaggc aggcggatca tgaggtcagg agatcaagac    3960
catcctggct aacacggtga aactccatct ctactaaaaa tacaaaaaaa atagccgggc    4020
gtggtggcag gcgcctgtag tcccagctac tggggaggct gaggcaggaa atggtgtca    4080 acccgggagg cggagcttgc agtgagccga gattgcgcca ctgcactcca gcctgggcaa    4140
tagagtgaga ctccgtctca aaaaaaaaaa aaaaaaaaa aacttcaaca ataccctcag    4200
gttgataatt ttggatatct atctgtatct atatatcttg tttacctggt ctccagaaaa    4260
agaacacata cacatatcca tatataaaat atgtatacat gtatcaaatc tacgtaaact    4320
ataaaggtgg gatggcttta attatggccc aagctactaa gacaatgaag acttttttggg    4380 gctgcaagct actgcttccc ttctttatct actagcctct taaacaaggc tcacttgtgc    4440
tacaagacag tccaccgttt tgtttttttt ttcttttttt tgagacaggg tctcactctt    4500
tcccaggctg cagtacagtg acacagtctc agctcactgc agctttgacc ttgccgggct    4560
caggtgaccc ttacacttca gcctcccaag tagcagggac tataggtgtg caccaacatg    4620
cttggttaat ttttgtattt tttgtagaga cagggttttg ccatgttgtc caggctagtc    4680
tcgaattcct gggctcaagt gattcacctg ccttggcctc ccaaagtgct aggattacag    4740
atgggagcca ccacgcccag cccagtccag ctcttatatg tagcacaggg aaaggacaaa    4800
tacttgtcaa ctataaataa gaaacattgc taatgcattg caaagaacac tagtttcatt    4860
tactttataa cttagatgtc tactgggtga gacgaatgtc tttgttcttt aaaaaatagg    4920
aaaagagaag aaaaactagc ataacataag tactcatttg taagactttc tgacatgtaa    4980
cattagttcc gtagttttga gacctggtag aactgacttt catatttgga taacctggaa    5040
```

```
aacacccaaa cacaaacttc aagtcttctt tctctttttt cattatcttt tttagtctga   5100
ggtgacacca tcattaagga ttcgacaccc gtttgtaaat aaaatgacat cagcaattac   5160
tctgaaatgt ttctagtttg caaagactta gcaatgtgat gttattaacc cttcctccct   5220
tcagagacct gtcctaagct ctgaaccact cattccttcc actcttctta ccccaggtgg   5280
ttgatgagca gtggtccctg tgttccaca  aagagtcatt aaagtgttac agctggtagc   5340
actggtagca aaaaacaaa  ccaaaaagta cacacagaca cacacacaca cacgcacaca   5400
tacacacaca cacgcacttg gccaagtgac aaaagcttgg cccctgaaat ttctatgaga   5460
tccgatgacc accaacatca aagcattttt tttttttttt ttttgagacg tagtctcgct   5520
ctgtcaccca ggctagagtg cagtggtgca atcacagctc actgcaacct ccacctcccg   5580
ggttcaagcg attctcctgc ctcagcctct cgagtagctg tgactacagg cacctgccac   5640
catgcccggc tatttttttg tatttttagt agagacgggg tttcaccgtg ttagccagga   5700
tggtcttgat ctcctgacct cgtgatccat ccgcctcggc ctcccaaatt gctgggatta   5760
caggcatgag ccaccacgcc cggcccatca aggaattgt  aacaactatt tgagagcact   5820
gacaataaga ttaacactcg gttgatttag atgttatgct ggtcctcagg cattcatctt   5880
tagatatttt tggggtggaa gtggggtagg gctgacttag taaaaataac ctcttagccc   5940
aaaggcttta ttcagactta caccgatttg aggggtgggg ttgtggaatg caaggttagg   6000
ttcttaccta atatttgatg actaatttag aattttaaat gtaattttaa attttagtga   6060
ctggtttcaa atctatttta acttctagat tgttcaaaga ggtctcagta catggctaca   6120
atcaaagtat tagactagct atttctcagc tcagtgctca gaaaaattat tactgttgat   6180
acctttttct ttgtttcctg ttaaataaat cacctcttta aagacagaaa aaaaaaaaa   6240 a                                                                 6241
```

<210> SEQ ID NO 8
<211> LENGTH: 2474
<212> TYPE: DNA
<213> ORGANISM: Homo sapiens

<400> SEQUENCE: 8

```
ggagattttg agcagaggct tcctaggctc cgtagaaatt tgcatacagc ttccacttcc     60
tgcttcagag cctgttcttc tacttacctg ggcccggaga aggtggaggg agacgagaag    120
ccgccgagag ccgactaccc tccgggccca gtctgtctgt ccgtggtgga tctaagcctc    180
atctgtatcc tcttgtgatg gcgtgaagga aagccatggc agatttccag cctggtgatg    240
ctgtacagaa cacaggtggc ctgcttccat gcctcctcag cttcaagaaa ctagaatgaa    300
ccgaagcatt cctgtggagg ttgatgaatc agaaccatac ccaagtcagt tgctgaaacc    360
aatcccagaa tattccccgg aagaggaatc agaaccacct gctccaaata taaggaacat    420
ggcacccaac agcttgtctg cacccacaat gcttcacaat tcctccggag acttttctca    480
agctcactca accctgaaac ttgcaaatca ccagcggcct gtatcccggc aggtcacctg    540
cctgcgcact caagttctgg aggacagtga agacagtttc tgcaggagac acccaggcct    600
gggcaaagct ttcccttctg ggtgctctgc agtcagcgag cctgcgtctg agtctgtggt    660
tggagccctc cctgcagagc atcagttttc atttatggaa aaacgtaatc aatggctggt    720
atctcagctt tcagcggctt ctcctgacac tggccatgac tcagacaaat cagaccaaag    780
tttacctaat gcctcagcag actccttggg cggtagccag gagatggtgc aacggcccca    840
```

```
gcctcacagg aaccgagcag gcctggatct gccaaccata gacacgggat atgattccca      900
gccccaggat gtcctgggca tcaggcagct ggaaaggccc ctgcccctca cctccgtgtg      960
ttaccccag gacctcccca gacctctcag gtccaggag ttccctcagt ttgaacctca       1020
gaggtatcca gcatgtgcac agatgctgcc tcccaatctt tccccacatg ctccatggaa     1080
ctatcattac cattgtcctg gaagtcccga tcaccaggtg ccatatggcc atgactaccc     1140
tcgagcagcc taccagcaag tgatccagcc ggctctgcct gggcagcccc tgcctggagc     1200
cagtgtgaga ggcctgcacc ctgtgcagaa ggttatcctg aattatccca gcccctggga     1260
ccacgaagag aggcccgcac agagagactg ctcctttccg gggcttccaa ggcaccagga     1320
ccagccacat caccagccac ctaatagagc tggtgctcct ggggagtcct ggagtgccc      1380
tgcagagctg agaccacagg ttccccagcc tccgtccca gctgctgtgc ctagacccc      1440
tagcaaccct ccagccagag aactctaaa acaagcaat ttgccagaag aattgcggaa       1500
agtctttatc acttattcga tggacacagc tatggaggtg gtgaaattcg tgaacttttt    1560
gttggtaaat ggcttccaaa ctgcaattga catatttgag gatagaatcc gaggcattga    1620
tatcattaaa tggatggagc gctaccttag ggataagacc gtgatgataa tcgtagcaat    1680
cagccccaaa tacaaacagg acgtggaagg cgctgagtcg cagctggacg aggatgagca    1740
tggcttacat actaagtaca ttcatcgaat gatgcagatt gagttcataa acaaggaag     1800
catgaatttc agattcatcc ctgtgctctt cccaaatgct aagaaggagc atgtgcccac    1860
ctggcttcag aacactcatg tctacagctg gcccaagaat aaaaaaaaca tcctgctgcg    1920
gctgctgaga gaggaagagt atgtggctcc tccacggggg cctctgccca ccttcaggt    1980
ggttcccttg tgacaccgtt catcccaga tcactgaggc caggccatgt ttggggcctt    2040
gttctgacag cattctggct gaggctggtc ggtagcactc ctggctggtt tttttctgtt    2100
cctccccgag aggccctctg gccccagga aactgttgt gcagagctct ccccggaga     2160
cctccacaca ccctggcttt gaagtggagt ctgtgactgc tctgcattct ctgcttttaa    2220
aaaaaccatt gcaggtgcca gtgtcccata tgttcctcct gacagtttga tgtgtccatt    2280
ctgggcctct cagtgcttag caagtagata atgtaaggga tgtggcagca aatggaaatg    2340
actacaaaca ctctcctatc aatcacttca ggctactttt atgagttagc cagatgcttg    2400
tgtatcctca gaccaaactg attcatgtac aaataataaa atgtttactc ttttgtaaaa    2460
aaaaaaaaaa aaaa                                                       2474
```

<210> SEQ ID NO 9
<211> LENGTH: 2819
<212> TYPE: DNA
<213> ORGANISM: Homo sapiens

<400> SEQUENCE: 9

```
tacaggcgtg agtcaccgcg ctcggcaatg ctgatgtttt aagcagttag aggaggtgga      60
agaagctcga ctccctcttc ttccccatta tctgcccaca atccctcct ttggagctgc     120
taatgattac taattcttaa cattcgagtt caatctcctc ccggagacac cctcccaggc    180
gagggcactg cgactacact gaggttctgc ccactcctgg gcagcttctt agctgggtgg    240
cgaaaacaaa aatgccgcct aattggtcac tggcccttc tcatgaatga aggaggtttc    300
tgttttaaga aataaagtga ctcctcagcc gttgattcac tgcccacagg gagatttga     360
gcagaggctt cctaggctcc gtagaaattt gcatacagct tccacttcct gcttcagagc   420
ctgttcttct acttacctgg gcccggagaa ggtggaggga gacgagaagc cgccgagagc  480
```

```
cgactaccct ccgggcccag tctgtctgtc cgtggtggat ctaagatgcc tctgcagcct    540
catctgtatc ctcttgtgat ggcgtgaagg aaagccatgg cagatttcca gcctggtgat    600
gctgtacaga acacaggtgg cctgcttcca tgcctcctca gcttcaagaa actagaatga    660
accgaagcat tcctgtggag gttgatgaat cagaaccata cccaagtcag ttgctgaaac    720
caatcccaga atattccccg gaagaggaat cagaaccacc tgctccaaat ataaggaaca    780
tggcacccaa cagcttgtct gcacccacaa tgcttcacaa ttcctccgga gacttttctc    840
aagctcactc aaccctgaaa cttgcaaatc accagcggcc tgtatcccgg caggtcacct    900
gcctgcgcac tcaagttctg gaggacagtg aagacagttt ctgcaggaga cacccaggcc    960
tgggcaaagc tttcccttct gggtgctctg cagtcagcga gcctgcgtct gagtctgtgg   1020
ttggagccct ccctgcagag catcagtttt catttatgga aaaacgtaat caatggctgg   1080

tatctcagct ttcagcggct tctcctgaca ctggccatga ctcagacaaa tcagaccaaa   1140
gtttacctaa tgcctcagca gactccttgg gcggtagcca ggagatggtg caacggcccc   1200
agcctcacag gaaccgagca ggcctggatc tgccaaccat agacacggga tatgattccc   1260 agcccccagga tgtcctgggc atcaggcagc тggaaaaggcc cctgcccctc acctccgtgt   1320
gttaccccca ggacctcccc agacctctca ggtccaggga gттсссстсag tttgaacctc   1380 agaggtatcc agcatgtgca cagatgctgc ctcccaatct ttcccacat gctccatgga   1440 actatcatta ccattgtcct ggaagtcccg atcaccaggt gccatatggc catgactacc   1500

ctcgagcagc ctaccagcaa gtgatccagc cggстсстgcс tgggcagccc ctgcctggag   1560
ccagtgtgag aggcctgcac cctgtgcaga aggttatcct gaattatccc agcccctggg   1620
accacgaaga gaggcccgca cagagagact gстсcттттcс ggggcttcca aggcaccagg   1680
accagccaca tcaccagcca cctaatagag ctggtgctcc tggggagtcc ttggagtgcc   1740

ctgcagagct gagaccacag gttccccagc ctccgtcccc agctgctgtg cctagacccc   1800

ctagcaaccc tccagccaga ggaactctaa aaacaagcaa tttgccagaa gaattgcgga   1860
aagtctttat cacttattcg atggacacag ctatggaggt ggtgaaattc gtgaacttt    1920

tgttggtaaa tggcttccaa actgcaattg acatatttga ggatagaatc cgaggcattg   1980

atatcattaa atggatggag cgctacctta gggataagac cgtgatgata atcgtagcaa   2040

tcagccccaa atacaaacag gacgtggaag cgctgagtc gcagctggac gaggatgagc   2100

atggcttaca tactaagtac атттcaтcgaa tgatgcagat tgagttcata aaacaaggaa   2160
gcatgaattt cagattcatc cctgtgctct tcccaaatgc taagaaggag catgtgccca   2220
cctggcttca gaacactcat gtctacagct ggcccaagaa taaaaaaaac атссstgcтgc   2280 ggctgctgag agaggaagag tatgtggctc ctcacgggg gcctctgccc acccttcagg   2340

tggttccctt gtgacaccgt tcatccccag atcactgagg ccaggccatg tttggggcct   2400

tgttctgaca gcattctggc tgaggctggt cggtagcact cctggctggt тттттттстgт   2460

tcctccccga gaggccctct ggcccccagg aaacctgttg tgcagagctc ttccccggag   2520
acctccacac accctggctt tgaagtggag tctgtgactg ctctgcattc tctgctttta   2580
aaaaaaccat tgcaggtgcc agtgtcccat atgttcctcc tgcagtttg atgtgtccat   2640

tctgggcctc tcagtgctta gcaagtagat aatgtaaggg atgtggcagc aaatggaaat   2700
gactacaaac actctcctat caatcacttc aggctacttt tatgagttag ccagatgctt   2760
gtgtatcctc agaccaaact gattcatgta caaataataa aatgtttact cttttgtaa   2819
```

<210> SEQ ID NO 10
<211> LENGTH: 6244
<212> TYPE: DNA
<213> ORGANISM: Homo sapiens

<400> SEQUENCE: 10

```
aatgctgatg ttttaagcag ttagaggagg tggaagaagc tcgactccct cttcttcccc    60
attatctgcc cacaatcccc tcctttggag ctgctaatga ttactaattc ttaacattcg   120
agttcaatct cctcccggag cacccctccc aggcgagggc actgcgacta cactgaggtt   180
ctgcccactc ctgggcagct tcttagctgg gtggcgaaaa caaaaatgcc gcctaattgg   240
tcactggccc tttctcatga atgaaggagg tttctgtttt aagaaataaa gtgactcctc   300
agccgttgat tcactgccca cagggagatt ttgagcagag gcttcctagg ctccgtagaa   360
atttgcatac agcttccact tcctgcttca gagcctgttc ttctacttac ctgggcccgg   420
agaaggtgga gggagacgag aagccgccga gagccgacta ccctccgggc ccagtctgtc   480
tgtccgtggt ggatctaaga aactagaatg aaccgaagca ttcctgtgga ggttgatgaa   540
tcagaaccat acccaagtca gttgctgaaa ccaatcccag aatattcccc ggaagaggaa   600
tcagaaccac ctgctccaaa tataaggaac atggcaccca acagcttgtc tgcacccaca   660
atgcttcaca attcctccgg agacttttct caagctcact caaccctgaa acttgcaaat   720
caccagcggc ctgtatcccg gcaggtcacc tgcctgcgca ctcaagttct ggaggacagt   780
gaagacagtt tctgcaggag acacccaggc ctgggcaaag cttteecttc tgggtgetet   840
gcagtcagcg agcctgcgtc tgagtctgtg gttggagccc tccctgcaga gcatcagttt   900
tcatttatgg aaaaacgtaa tcaatggctg gtatctcagc tttcagcggc ttctcctgac   960
actggccatg actcagacaa atcagaccaa agtttaccta atgcctcagc agactccttg  1020
ggcggtagcc aggagatggt gcaacggccc cagcctcaca ggaaccgagc aggcctggat  1080
ctgccaacca tagacacggg atatgattcc cagcccagg atgtcctggg catcaggcag  1140
ctggaaaggc ccctgcccct cacctccgtg tgttaccccc aggacctccc cagacctctc  1200
aggtccaggg agttccctca gtttgaacct cagaggtatc cagcatgtgc acagatgctg  1260
cctcccaatc tttccccaca tgctccatgg aactatcatt accattgtcc tggaagtccc  1320
gatcaccagg tgccatatgg ccatgactac cctcgagcag cctaccagca agtgatccag  1380
ccggctctgc ctgggcagcc cctgcctgga gccagtgtga gaggcctgca ccctgtgcag  1440
aaggttatcc tgaattatcc cagccctgg gaccacgaag agaggcccgc acagagagac  1500
tgctcctttc cggggcttcc aaggcaccag gaccagccac atcaccagcc acctaataga  1560
gctggtgctc ctggggagtc cttggagtgc cctgcagagc tgagaccaca ggttccccag  1620
cctccgtccc cagctgctgt gcctagaccc cctagcaacc ctccagccag aggaactcta  1680
aaaacaagca atttgccaga agaattgcgg aaagtcttta tcacttattc gatggacaca  1740
gctatggagg tggtgaaatt cgtgaacttt ttgttggtaa atggcttcca aactgcaatt  1800
gacatatttg aggatagaat ccgaggcatt gatatcatta aatggatgga gcgctacctt  1860
agggataaga ccgtgatgat aatcgtagca atcagcccca atacaaaca ggacgtggaa  1920
ggcgctgagt cgcagctgga cgaggatgag catggcttac atactaagta cattcatcga  1980
atgatgcaga ttgagttcat aaaacaagga agcatgaatt tcagattcat ccctgtgctc  2040
ttcccaaatg ctaagaagga gcatgtgccc acctggcttc agaacactca tgtctacagc  2100
tggcccaaga ataaaaaaaa catcctgctg cggctgctga gagaggaaga gtatgtggct  2160
```

```
cctccacggg ggcctctgcc caccctteag gtggttccct tgtgacaccg ttcatccca      2220
gatcactgag gccaggccat gtttggggcc ttgttctgac agcattctgg ctgaggctgg      2280
tcggtagcac tcctggctgg ttttttttctg ttcctccccg agaggccctc tggccccag     2340
gaaacctgtt gtgcagagct cttccccgga gacctccaca caccctggct ttgaagtgga      2400
gtctgtgact gctctgcatt tctgctttt aaaaaaacca ttgcaggtgc cagtgtccca      2460
tatgttcctc ctgacagttt gatgtgtcca ttctgggcct ctcagtgctt agcaagtaga      2520
taatgtaagg gatgtggcag caaatggaaa tgactacaaa cactctccta tcaatcactt      2580
caggctactt ttatgagtta gccagatgct tgtgtatcct cagaccaaac tgattcatgt      2640
acaaataata aaatgtttac tcttttgtaa gattatgttt tacttatctc aaaggagata      2700
catataattt ataatgatat gggcagttgc ttccagggac atcaacaaag ctgcttagat      2760
ataatattag ataaatataa cagaccactc tgtattaatg gattaaagcc agctagttaa      2820
acaaccctt ttaaccataa tcatggaagc tttattcttg caataaagat ttttaggctg      2880
ggcgcagtga ctcacacctg taatcccagc actttgggaa gctaaggcag gcagatcatt      2940
tgaggtcagg agtttgagac cagcctggcc aacatggtga acccccatct ctgctaaaat      3000
tacaaaaaag ttagccgggc atggtggtgt gcacctgtaa tcccagctac tcgggaggct      3060
gaggcaggag aatcacttga acccgggagg cagaggttgc agtgagccga gatcatgtca      3120
ctgcactcta gcttgggaga cagagcgaga ctccgtctca aaaacaaac aaacaaataa       3180
aaacacccat ttttaacaaa acaactttat atagcataca gccatgattc taaatagtat      3240
gattatggtt ctcaggatct gactacatag gtaaaaatat ttgcatatgt gtatgaagtg      3300
ttgggggatg taggctagaa ttgtagtctg tgttctaatt ttggttctac caccaattag      3360
ctgtatgacc tttagcaagt cctttaactt ttcttagatt ccagggactc atttataaaa      3420
tgacatggac aaaagcatct ctaatcactc taaaagattt gaagtctagg acctaaattc      3480
taaatactct tttgaggagt gactgagttt tcattttcat aattatgtct ctcagaggac      3540
aaatttacat tttcttaaca gagacatttt cttcttcttt ttttttgttt gagacagagt      3600
ctcgctctgt cgtccaggct ggagtgcagt gctgcaatct tggctcactg caacctgcgc      3660
ctcctgggtt caagtgattc ttctgcctca acctcccaag tagctagacc tataggcgcc      3720
tgccaccatg cccagctaat ttttgtattt ttagtagaga cagggtttca tattggccag      3780
actggtctcg aactcctgac cttgtgatcc gcccacctcg gcctcccaaa gtgctgggat      3840
tacaggtgtg agccaccaca cccagccaac attttcctct tttaaaaaat atcttctcac      3900
gcctgtaatc ccagcacttt gggaggctga ggcaggcgga tcatgaggtc aggagatcaa      3960
gaccatcctg gctaacacgg tgaaactcca tctctactaa aaatacaaaa aaatagccg       4020
ggcgtggtgg caggcgcctg tagtcccagc tactggggag gctgaggcag gaaaatggtg      4080
tcaacccggg aggcggagct tgcagtgagc cgagattgcg ccactgcact ccagcctggg      4140
caatagagtg agactccgtc tcaaaaaaaa aaaaaaaaa aaaacttca acaataccct        4200
caggttgata atttttggata tctatctgta tctatatatc ttgtttacct ggtctccaga     4260
aaaagaacac atacacatat ccatatataa aatatgtata catgtatcaa atctacgtaa      4320
actataaagg tgggatggct ttaattatgg cccaagctac taagacaatg aagactttt       4380
ggggctgcaa gctactgctt cccttctta tctactagcc tcttaaacaa ggctcacttg       4440
tgctacaaga cagtccaccg ttttgttttt tttttctttt tttgagaca gggtctcact       4500
```

```
ctttcccagg ctgcagtaca gtgacacagt ctcagctcac tgcagctttg accttgccgg    4560
gctcaggtga cccttacact tcagcctccc aagtagcagg gactataggt gtgcaccaac    4620
atgcttggtt aattttttgta ttttttgtag agacagggtt ttgccatgtt gtccaggcta   4680
gtctcgaatt cctgggctca agtgattcac ctgccttggc ctcccaaagt gctaggatta    4740
cagatgggag ccaccacgcc cagcccagtc cagctcttat atgtagcaca gggaaaggac    4800
aaatacttgt caactataaa taagaaacat tgctaatgca ttgcaaagaa cactagtttc    4860
atttacttta taacttagat gtctactggg tgagacgaat gtctttgttc tttaaaaaat    4920
aggaaaagag aagaaaaact agcataacat aagtactcat ttgtaagact ttctgacatg    4980
taacattagt tccgtagttt tgagacctgg tagaactgac tttcatattt ggataacctg    5040
gaaaacaccc aaaacaaaac ttcaagtctt ctttctcttt tttcattatc tttttagtc     5100 tgaggtgaca ccatcattaa ggattcgaca cccgtttgta aataaaatga catcagcaat    5160
tactctgaaa tgtttctagt ttgcaaagac ttagcaatgt gatgttatta acccttcctc    5220
ccttcagaga cctgtcctaa gctctgaacc actcattcct tccactcttc ttaccccagg    5280
tggttgatga gcagtggtcc ctggtgttcc acaaagagtc attaaagtgt tacagctggt    5340
agcactggta gcaaaaaaac aaccaaaaa gtacacacac acacacacac acacgcac      5400 acatacacac acacacgcac ttggccaagt gacaaaagct tggcccctga aatttctatg    5460
agatccgatg accaccaaca tcaaagcatt tttttttttt tttttttgag acgtagtctc    5520
gctctgtcac ccaggctaga gtgcagtggt gcaatcacag ctcactgcaa cctccacctc    5580
ccgggttcaa gcgattctcc tgcctcagcc tctcgagtag ctgtgactac aggcacctgc    5640
caccatgccc ggctaatttt ttgtattttt agtagagacg gggtttcacc gtgttagcca    5700
ggatggtctt gatctcctga cctcgtgatc catccgcctc ggcctcccaa attgctggga    5760
ttacaggcat gagccaccac gcccggccca tcaaggaat tgtaacaact atttgagagc     5820
actgacaata agattaacac tcggttgatt tagatgttat gctggtcctc aggcattcat    5880
ctttagatat ttttggggtg gaagtggggt agggctgact tagtaaaaat aacctcttag    5940
cccaaaggct ttattcagac ttcacccgat ttgaggggtg ggtttgtgga atgcaaggtt    6000
aggttcttac ctaatatttg atgactaatt tagaattta aatgtaattt taaattttag     6060
tgactggttt caaatctatt ttaacttcta gattgttcaa agaggtctca gtacatggct    6120
acaatcaaag tattagacta gctatttctc agctcagtgc tcagaaaaat tattactgtt    6180 gataccttt tctttgtttc ctgttaaata aatcacctct ttaaagacag aaaaaaaaaa     6240
aaaa                                                                 6244

<210> SEQ ID NO 11
<211> LENGTH: 909
<212> TYPE: DNA
<213> ORGANISM: Homo sapiens

<400> SEQUENCE: 11
ggctgcttct tttggaggga gccagtgggg gacgggagtc tcagcaggct ggggtgttgc      60
acttttcctt ttgtctgcag cctgatgttt gctttgtgct gaaggaagac cgtgatgata     120
atcgtagcaa tcagccccaa atacaaacag gacgtggaag gcgctgagtc gcagctggac     180
gaggatgagc atggcttaca tactaagtac attcatcgaa tgatgcagat tgagttcata     240
aaacaaggaa gcatgaattt cagattcatc cctgtgctct tcccaaatgc taagaaggag     300
catgtgccca cctggcttca gaacactcat gtctacagct ggcccaagaa taaaaaaaac    360
```

```
atcctgctgc ggctgctgag agaggaagag tatgtggctc ctccacgggg gcctctgccc      420
acccttcagg tggttccctt gtgacaccgt tcatccccag atcactgagg ccaggccatg      480
tttggggcct tgttctgaca gcattctggc tgaggctggt cggtagcact cctggctggt      540
ttttttctgt tcctccccga gaggccctct ggccccagg  aaacctgttg tgcagagctc      600
ttccccggag acctccacac accctggctt tgaagtggag tctgtgactg ctctgcattc      660
tctgctttta aaaaaccat  tgcaggtgcc agtgtcccat atgttcctcc tgacagtttg      720
atgtgtccat tctgggcctc tcagtgctta gcaagtagat aatgtaaggg atgtggcagc      780
aaatggaaat gactacaaac actctcctat caatcacttc aggctacttt tatgagttag      840
ccagatgctt gtgtatcctc agaccaaact gattcatgta caaataataa aatgtttact      900
cttttgtaa                                                             909

<210> SEQ ID NO 12
<211> LENGTH: 4523
<212> TYPE: DNA
<213> ORGANISM: Homo sapiens

<400> SEQUENCE: 12
ataggaaaga aggaaatgaa ggcggagagt ggggagagag cagcagaatt caatttaatc       60
tgaggccacc ccaagtgttt tgtagaattg ggctgaagag gtttcctagg cagcctcgca      120
ggctgcacag cacaccaccc ccgagaagac cgtgatgata atcgtagcaa tcagccccaa      180
atacaaacag gacgtggaag gcgctgagtc gcagctggac gaggatgagc atggcttaca      240
tactaagtac attcatcgaa tgatgcagat tgagttcata aaacaaggaa gcatgaattt      300
cagattcatc cctgtgctct tcccaaatgc taagaaggag catgtgccca cctggcttca      360
gaacactcat gtctacagct ggcccaagaa taaaaaaaac atcctgctgc ggctgctgag      420
agaggaagag tatgtggctc ctccacgggg gcctctgccc acccttcagg tggttccctt      480
gtgacaccgt tcatccccag atcactgagg ccaggccatg tttggggcct tgttctgaca      540
gcattctggc tgaggctggt cggtagcact cctggctggt ttttttctgt tcctccccga      600
gaggccctct ggccccagg  aaacctgttg tgcagagctc ttccccggag acctccacac      660
accctggctt tgaagtggag tctgtgactg ctctgcattc tctgctttta aaaaaccat       720 tgcaggtgcc agtgtcccat atgttcctcc tgacagtttg atgtgtccat tctgggcctc      780
tcagtgctta gcaagtagat aatgtaaggg atgtggcagc aaatggaaat gactacaaac      840
actctcctat caatcacttc aggctacttt tatgagttag ccagatgctt gtgtatcctc      900
agaccaaact gattcatgta caaataataa aatgtttact cttttgtaag attatgtttt      960
acttatctca aaggagatac atataattta taatgatatg ggcagttgct tccagggaca     1020
tcaacaaagc tgcttagata taatattaga taaatataac agaccactct gtattaatgg     1080
attaaagcca gctagttaaa caaccctttt taaccataat catggaagct ttattcttgc     1140
aataaagatt tttaggctgg gcgcagtgac tcacacctgt aatcccagca ctttgggaag     1200
ctaaggcagg cagatcattt gaggtcagga gtttgagacc agcctggcca acatggtgaa     1260
accccatctc tgctaaaatt acaaaaaagt tagccgggca tggtggtgtg cacctgtaat     1320
cccagctact cgggaggctg aggcaggaga atcacttgaa cccgggaggc agaggttgca     1380
gtgagccgag atcatgtcac tgcactctag cttgggagac agagcgagac tccgtctcaa     1440
aaaacaaaca aacaaataaa aacacccatt tttaacaaaa caactttata tagcatacag     1500
```

-continued

```
ccatgattct aaatagtatg attatggttc tcaggatctg actacatagg taaaaatatt    1560
tgcatatgtg tatgaagtgt tgggggatgt aggctagaat tgtagtctgt gttctaatt     1620
tggttctacc accaattagc tgtatgacct ttagcaagtc ctttaacttt tcttagattc    1680
cagggactca tttataaaat gacatggaca aaagcatctc taatcactct aaaagatttg    1740
aagtctagga cctaaattct aaatactctt ttgaggagtg actgagtttt cattttcata    1800
attatgtctc tcagaggaca aatttacatt ttcttaacag agacattttc ttcttctttt    1860
tttttgtttg agacagagtc tcgctctgtc gtccaggctg gagtgcagtg ctgcaatctt    1920
ggctcactgc aacctgcgcc tcctgggttc aagtgattct tctgcctcaa cctcccaagt    1980
agctagacct ataggcgcct gccaccatgc ccagctaatt tttgtatttt tagtagagac    2040
agggtttcat attggccaga ctggtctcga actcctgacc ttgtgatccg cccacctcgg    2100
cctcccaaag tgctgggatt acaggtgtga gccaccacac ccagccaaca ttttcctctt    2160
ttaaaaaata tcttctcacg cctgtaatcc cagcactttg ggaggctgag gcaggcggat    2220
catgaggtca ggagatcaag accatcctgg ctaacacggt gaaactccat ctctactaaa    2280
aatacaaaaa aaatagccgg gcgtggtggc aggcgcctgt agtcccagct actggggagg    2340
ctgaggcagg aaaatggtgt caacccggga ggcggagctt gcagtgagcc gagattgcgc    2400
cactgcactc cagcctgggc aatagagtga gactccgtct caaaaaaaaa aaaaaaaaa     2460
aaaacttcaa caatacccct caggttgataa ttttggatat ctatctgtat ctatatatct   2520
tgtttacctg gtctccagaa aaagaacaca tacacatatc catatataaa atatgtatac    2580
atgtatcaaa tctacgtaaa ctataaaggt gggatggctt taattatggc ccaagctact    2640
aagacaatga agacttttg gggctgcaag ctactgcttc ccttctttat ctactagcct     2700
cttaaacaag gctcacttgt gctacaagac agtccaccgt tttgttttt ttttcttttt     2760
tttgagacag ggtctcactc tttcccaggc tgcagtacag tgacacagtc tcagctcact    2820
gcagctttga ccttgccggg ctcaggtgac ccttacactt cagcctccca agtagcaggg    2880
actataggtg tgcaccaaca tgcttggtta attttttgtat tttttgtaga cagggtttt    2940
tgccatgttg tccaggctag tctcgaattc ctgggctcaa gtgattcacc tgccttggcc    3000
tcccaaagtg ctaggattac agatgggagc caccacgccc agcccagtcc agctcttata    3060
tgtagcacag ggaaaggaca aatacttgtc aactataaat aagaaacatt gctaatgcat    3120
tgcaaagaac actagtttca tttactttat aacttagatg tctactgggt gagacgaatg    3180
tctttgttct ttaaaaaata ggaaaagaga agaaaaacta gcataacata agtactcatt    3240
tgtaagactt tctgacatgt aacattagtt ccgtagtttt gagacctggt agaactgact    3300
ttcatatttg gataacctgg aaaacaccca aacacaaact tcaagtcttc tttctctttt    3360
ttcattatct ttttagtctc gaggtgacac catcattaag gattcgacac ccgtttgtaa    3420
ataaaatgac atcagcaatt actctgaaat gtttctagtt tgcaaagact tagcaatgtg    3480
atgttattaa cccttcctcc cttcagagac ctgtcctaag ctctgaacca ctcattcctt    3540
ccactcttct taccccaggt ggttgatgag cagtggtccc tggtgttcca caagagtca    3600
ttaaagtgtt acagctggta gcactggtag caaaaaaaca aaccaaaaag tacacacaga    3660
cacacacaca cacacgcaca catacacaca cacacgcact tggccaagtg acaaaagctt    3720
ggccctgaa atttctatga gatccgatga ccaccaacat caaagcatt ttttttttt      3780
tttttgaga cgtagtctcg ctctgtcacc caggctagag tgcagtggtg caatcacagc    3840
tcactgcaac ctccacctcc cgggttcaag cgattctcct gcctcagcct ctcgagtagc    3900
```

-continued

```
tgtgactaca ggcacctgcc accatgcccg gctaatttttt tgtattttta gtagagacgg    3960
ggtttcaccg tgttagccag gatggtcttg atctcctgac ctcgtgatcc atccgcctcg    4020
gcctcccaaa ttgctgggat tacaggcatg agccaccacg cccggcccat caaggaatt     4080 gtaacaacta tttgagagca ctgacaataa gattaacact cggttgattt agatgttatg    4140
ctggtcctca ggcattcatc tttagatatt tttggggtgg aagtggggta gggctgactt    4200
agtaaaaata acctcttagc ccaaaggctt tattcagact tacaccgatt tgaggggtgg    4260
gtttgtggaa tgcaaggtta ggttcttacc taatatttga tgactaattt agaattttaa    4320
atgtaatttt aaattttagt gactggtttc aaatctattt taacttctag attgttcaaa    4380
gaggtctcag tacatggcta caatcaaagt attagactag ctatttctca gctcagtgct    4440
cagaaaaatt attactgttg ataccttttt ctttgtttcc tgttaaataa atcacctctt    4500
taaagacaga aaaaaaaaaa aaa                                            4523
```

<210> SEQ ID NO 13
<211> LENGTH: 30
<212> TYPE: DNA
<213> ORGANISM: Artificial Sequence
<220> FEATURE:
<223> OTHER INFORMATION: Methylated sequence

<400> SEQUENCE: 13
mgmgmumgmg gcacatgctc mcmumumcmu                                       30

<210> SEQ ID NO 14
<211> LENGTH: 26
<212> TYPE: DNA
<213> ORGANISM: Artificial Sequence
<220> FEATURE:
<223> OTHER INFORMATION: Methylated sequence

<400> SEQUENCE: 14
mamgmumgmc taccgaccag mcmcmu                                           26

<210> SEQ ID NO 15
<211> LENGTH: 30
<212> TYPE: DNA
<213> ORGANISM: Artificial Sequence
<220> FEATURE:
<223> OTHER INFORMATION: Methylated sequence

<400> SEQUENCE: 15
mgmgmcmcmu ctcttcgtgg mumcmcmcma                                       30

<210> SEQ ID NO 16
<211> LENGTH: 30
<212> TYPE: DNA
<213> ORGANISM: Artificial Sequence
<220> FEATURE:
<223> OTHER INFORMATION: Methylated sequence

<400> SEQUENCE: 16
mamumgmcmc tcggattcta mumcmcmumc                                       30

<210> SEQ ID NO 17
<211> LENGTH: 30
<212> TYPE: DNA
<213> ORGANISM: Artificial Sequence
<220> FEATURE:
<223> OTHER INFORMATION: Methylated sequence

```
<400> SEQUENCE: 17
mgmumumgmc accatctcct mgmgmcmuma                                30

<210> SEQ ID NO 18
<211> LENGTH: 30
<212> TYPE: DNA
<213> ORGANISM: Artificial Sequence
<220> FEATURE:
<223> OTHER INFORMATION: Methylated sequence

<400> SEQUENCE: 18
mumgmgmumg atgtggctgg mumcmcmumg                                30
```